United States Patent
Roswech

(10) Patent No.: US 10,797,567 B2
(45) Date of Patent: Oct. 6, 2020

(54) ROTOR ASSEMBLY INCLUDING A HOUSING FOR A SENSOR ARRAY COMPONENT AND METHODS FOR USING SAME

(71) Applicant: LIFE TECHNOLOGIES CORPORATION, Carlsbad, CA (US)

(72) Inventor: Todd Roswech, Westbrook, CT (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 706 days.

(21) Appl. No.: 15/216,991

(22) Filed: Jul. 22, 2016

(65) Prior Publication Data
US 2017/0025930 A1  Jan. 26, 2017

Related U.S. Application Data

(60) Provisional application No. 62/195,937, filed on Jul. 23, 2015.

(51) Int. Cl.
*H02K 11/20* (2016.01)
*H02K 5/10* (2006.01)
(Continued)

(52) U.S. Cl.
CPC .......... *H02K 11/20* (2016.01); *B01L 3/50273* (2013.01); *B01L 3/502738* (2013.01);
(Continued)

(58) Field of Classification Search
CPC .... B01L 3/502; B01L 3/5027; B01L 3/50273; B01L 3/502753; B01L 3/50825;
(Continued)

(56) References Cited

U.S. PATENT DOCUMENTS 6,605,474 B1 *  8/2003  Cole .................... B01D 1/0029
                                                             159/44
9,914,968 B2 *  3/2018  Chiang ................ B01L 3/502
(Continued)

FOREIGN PATENT DOCUMENTS

EP           2400039      12/2011
WO      2017/015653 B1    1/2017

OTHER PUBLICATIONS

PCT/US2016/043823, International Search Report and Written Opinion dated Dec. 19, 2016, 16 pp.
(Continued)

*Primary Examiner* — Brian R Gordon

(57) ABSTRACT

A rotor assembly includes a rotor plate to rotate around a first axis, a bucket attached to the rotor plate and to rotate around a second axis, and a stop plate to rotate around the first axis between an open position and a closed position. When in the closed position, the stop plate engages the bucket to fix an angular position of the bucket relative to a plane of rotation of the rotor assembly. The rotor assembly further includes a housing for a sensor array component, the housing disposed in the bucket and including a solution inlet, a solution outlet, a transfer basin, a solution retainer disposed between the solution outlet and the transfer basin, and a collection reservoir in fluid communication with the transfer basin. The solution inlet and the solution outlet to engage ports of a flow cell of a sensor array.

9 Claims, 20 Drawing Sheets

(51) Int. Cl.
*B01L 3/00* (2006.01)
*B04B 5/04* (2006.01)
*F16K 99/00* (2006.01)
*C12Q 1/6874* (2018.01)
*B04B 11/04* (2006.01)
*G01N 35/00* (2006.01)
*G01N 35/04* (2006.01)

(52) U.S. Cl.
CPC .......... *B04B 5/0421* (2013.01); *C12Q 1/6874* (2013.01); *F16K 99/0013* (2013.01); *H02K 5/10* (2013.01); *B01L 2200/0668* (2013.01); *B01L 2200/10* (2013.01); *B01L 2300/0636* (2013.01); *B01L 2300/0663* (2013.01); *B01L 2300/0803* (2013.01); *B01L 2400/043* (2013.01); *B01L 2400/0409* (2013.01); *B01L 2400/0633* (2013.01); *B04B 2011/046* (2013.01); *F16K 2099/0084* (2013.01); *G01N 2035/00158* (2013.01); *G01N 2035/00495* (2013.01); *G01N 2035/0449* (2013.01)

(58) Field of Classification Search
CPC ..... B01L 2300/0803; B01L 2300/0819; B01L 2300/061; B01L 2300/08; B01L 3/50; B04B 5/0421; B04B 5/0442; G01N 2035/0449; G01N 2035/0439; G01N 2035/0444; G01N 2035/00495; G01N 2035/00158; G01N 21/05; G01N 21/07; G01N 2021/0357; G01N 21/03
See application file for complete search history.

(56) References Cited

U.S. PATENT DOCUMENTS

| | | | |
|---|---|---|---|
| 10,190,165 B2* | 1/2019 | Chiang | B01L 3/502 |
| 2005/0095172 A1* | 5/2005 | Nagaoka | B01L 3/502738 |
| | | | 422/72 |
| 2006/0013742 A1 | 1/2006 | Bahatt et al. | |
| 2010/0297659 A1* | 11/2010 | Yoo | G01N 35/00029 |
| | | | 435/6.16 |
| 2011/0020194 A1* | 1/2011 | Lee | B01L 3/50273 |
| | | | 422/400 |
| 2013/0023060 A1* | 1/2013 | Klaunik | B01L 3/502715 |
| | | | 436/501 |
| 2013/0236376 A1* | 9/2013 | Augstein | B01L 3/502723 |
| | | | 422/506 |
| 2014/0087958 A1* | 3/2014 | Chiang | B01L 3/502 |
| | | | 506/9 |
| 2014/0113366 A1* | 4/2014 | Dahan | B01L 3/502761 |
| | | | 435/309.1 |
| 2014/0212992 A1 | 7/2014 | Clime et al. | |
| 2015/0275292 A1* | 10/2015 | Chiang | B01L 3/502 |
| | | | 506/9 |

OTHER PUBLICATIONS

PCTUS2016043823, Invitation to Pay Additional Fees and Partial International Search Report dated Oct. 25, 2016, 7 pp.
PCT/US2016043823, International Preliminary Report on Patentability, dated Jan. 23, 2018, 1-10.

* cited by examiner

ROTOR ASSEMBLY INCLUDING A HOUSING FOR A SENSOR ARRAY COMPONENT AND METHODS FOR USING SAME

CROSS-REFERENCE TO RELATED APPLICATION(S)

This application claims benefit of U.S. Provisional Application No. 62/195,937, filed Jul. 23, 2015, and entitled "LIQUID GUIDE AND METHOD OF USE," which is incorporated herein by reference in its entirety.

FIELD OF THE DISCLOSURE

This disclosure, in general, relates to rotor assemblies and methods for using such rotor assemblies.

BACKGROUND

In fields such as chemistry, molecular biology, and biomedical sciences, researchers increasingly rely on small-scale sensor arrays for conducting testing. In particular, analytes, particularly analytes attached to beads or particle substrates, are deposited onto the small-scale sensor arrays for testing. As the number of sensors increases and the size of the individual sensors in the sensor array decreases, depositing analytes into the sensor array is increasingly difficult. Factors such as Brownian motion become increasingly dominant over gravity.

Therefore, an improved rotor assembly would be desirable.

SUMMARY

In a first aspect, a fluid transfer housing to engage a sensor array having a flow cell includes a solution inlet and a solution outlet to engage ports of the flow cell; a transfer basin; a solution retainer disposed between the solution outlet and the transfer basin; and a collection reservoir in fluid communication with the transfer basin.

In a second aspect, a rotor assembly includes a rotor plate to rotate around a first axis; a bucket rotatably attached to the rotor plate and to rotate around a second axis; and a stop plate to rotate around the first axis relative to the rotor plate between an open position and a closed position. When in the closed position, the stop plate is to engage the bucket to fix an angular position of the bucket relative to a plane of rotation of the rotor assembly. The rotor assembly further includes a housing for a sensor array component. The housing is disposed in the bucket and includes a solution inlet, a solution outlet, a transfer basin, a solution retainer disposed between the solution outlet and the transfer basin, and a collection reservoir in fluid communication with the transfer basin. The solution inlet and the solution outlet engage ports of a flow cell of a sensor array.

In a third aspect, a method of loading a sensor array component includes applying a solution to a sensor array component located within a housing that includes a solution inlet, a solution outlet, a solution retainer, a transfer basin, and a collection reservoir disposed in a bucket of a rotor assembly when a stop plate of the rotor assembly is in a closed position. The method further includes spinning the rotor assembly, the bucket rotating to a horizontal or negative angle relative to a plane of rotation of the rotor assembly, and the solution flowing out of the fluid outlet, over the solution retainer, and into the transfer basin. The method also includes moving the stop plate to an open position and spinning the rotor assembly, the bucket rotating to a positive angle relative to the plane of rotation of the rotor assembly, and the solution flowing from the transfer basin into the collection reservoir. The method optionally includes removing the solution from the collection reservoir.

This invention has many advantages, including the ability to retain the solution in the collection reservoir, enabling the removal of the solution from the collection reservoir after spinning the rotor assembly.

BRIEF DESCRIPTION OF THE DRAWINGS

The present disclosure may be better understood, and its numerous features and advantages made apparent to those skilled in the art by referencing the accompanying drawings.

The use of the same reference symbols in different drawings indicates similar or identical items.

DETAILED DESCRIPTION

Figure 1:
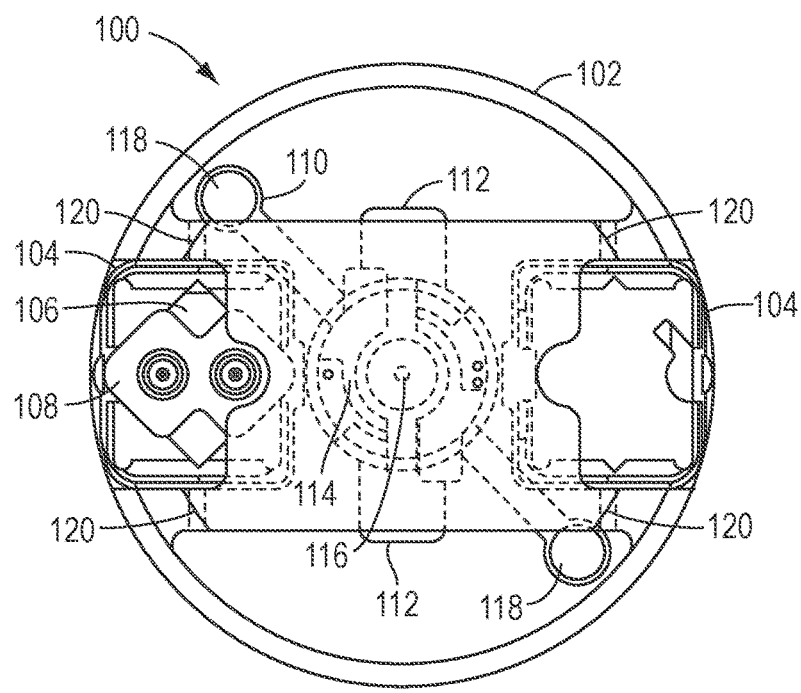
FIG. 1 and FIG. 2 include illustrations of an exemplary rotor assembly.
Figure 2:
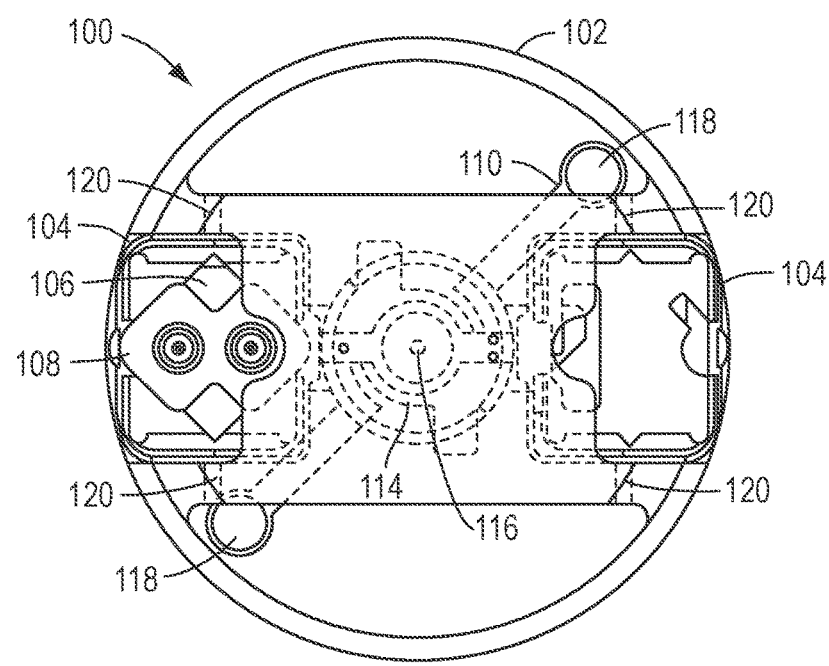

In an exemplary embodiment illustrated in FIG. 1 and FIG. 2, a rotor assembly 100 can rotate or spin around a central axis 116. In an example, the rotor assembly 100 can includes a rotor plate 102, which includes axles 120 to engage one or more buckets 104. In the illustrated example, the rotor plate 102 is configured to receive two buckets 104. Alternatively, the rotor assembly and rotor plate 102 can be configured to receive at least one bucket, such as at least two buckets, at least four buckets, or at least six buckets, but not greater than 20 buckets. The buckets 104 are configured to receive a sensor array component 106 and an associated cap 108. The cap 108 can assist with supplying a solution to or retrieving a solution from the sensor array component 106.

The rotor assembly 100 can further include a stop plate 110. The stop plate 110 can include wings 112 to engage the buckets 104, limiting rotation of the buckets around axles 120. The stop plate 110 can further include rings 118 that can be engaged, for example, by a tip of a pipetting robot. Using a pipetting robot and optionally the associated centrifuge motor, the stop plate 110 can be rotated around the central axis 116 or relative to the rotor plate 102, moving the wings 112 from an open position as illustrated in FIG. 1 to a closed position as illustrated in FIG. 2 in which the wings 112 engage the buckets 104 and limit the rotation the buckets 104 around the axles 120.

In addition, the rotor assembly 100 can include a coupler 114 to secure the rotor assembly 100 to the central axis 116 of a centrifuge motor.

Figure 3:
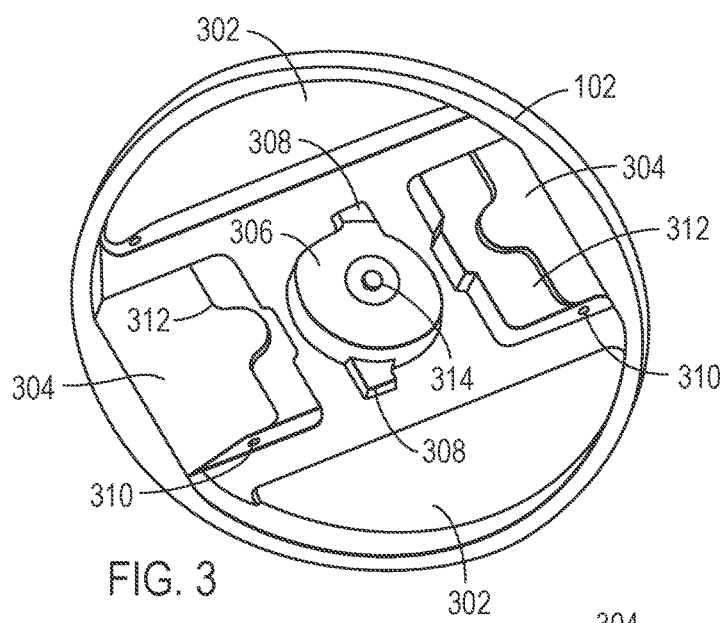
FIG. 3, FIG. 4, and FIG. 5 include illustrations of an exemplary rotor plate.
Figure 4:
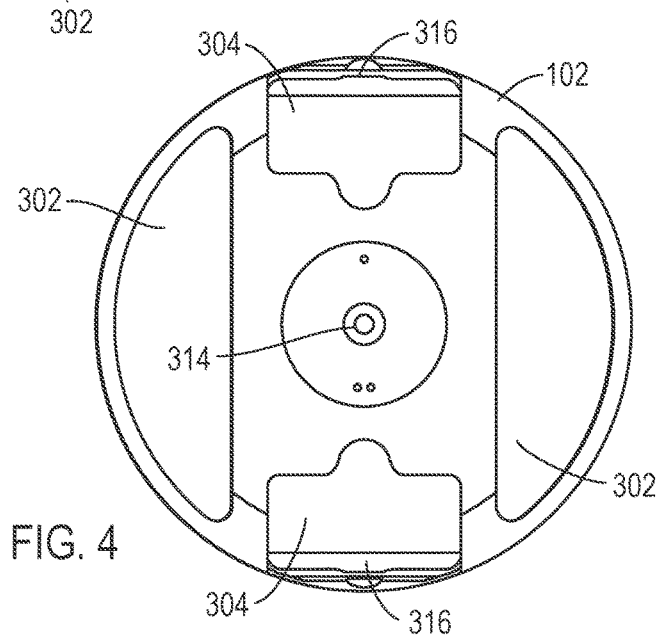
Figure 5:
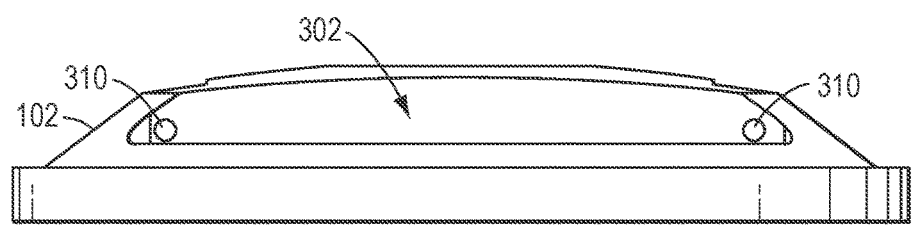

As illustrated in FIG. 3, FIG. 4, and FIG. 5, an exemplary rotor plate 102 includes openings 304 to receive buckets 104. In particular, the rotor plate 102 includes recesses 310 to receive axles 120 that are to engage the buckets 104 (illustrated in FIG. 1 and FIG. 2). The axles 120 can extend into the openings 304 and engage buckets. The rotor plate 102 also includes openings 302 through which stop plate rings 118 (illustrated in FIG. 1 and FIG. 2) can be engaged, for example, by a pipetting robot. The rotor plate 102 includes a central recess 306 to engage the stop plate 110 and the coupler 114 (illustrated in FIG. 1 and FIG. 2). Optionally, the central recess 306 can include slots 308 to engage wings (e.g., wings 1012 illustrated in FIG. 9 and FIG. 10) of a coupler 114 and limit relative motion of the coupler 114 and the rotor plate 102 (illustrated in FIG. 1 and FIG. 2). In particular, when the coupler 114 is rotated, the wings sufficiently engage the slots 308 and cause the rotor plate 102 to move with the coupler 114 with limited play. The rotor plate 102 can also include a central bore 314 to receive the fitting.

In proximity to the bucket opening 304 of the rotor plate 102, the rotor plate 102 can include an upper stop surface 312 and a rear stop surface 316. When a stop plate 110 is in a closed position, the stop plate 102 can force a bucket 104 or sensor array component into contact with the upper stop surface 312 or the backstop surface 316, limiting rotation of the bucket around the axles 120 engaging the recesses 310.

Figure 6:
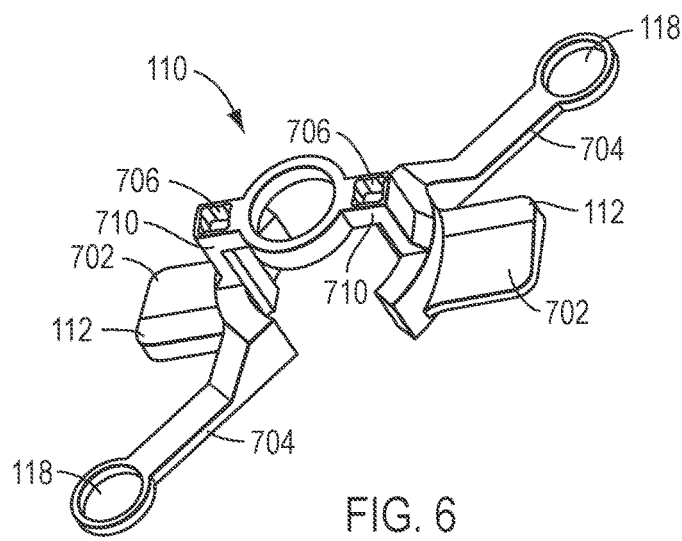
FIG. 6, FIG. 7, and FIG. 8 include illustrations of an exemplary stop plate.
Figure 7:
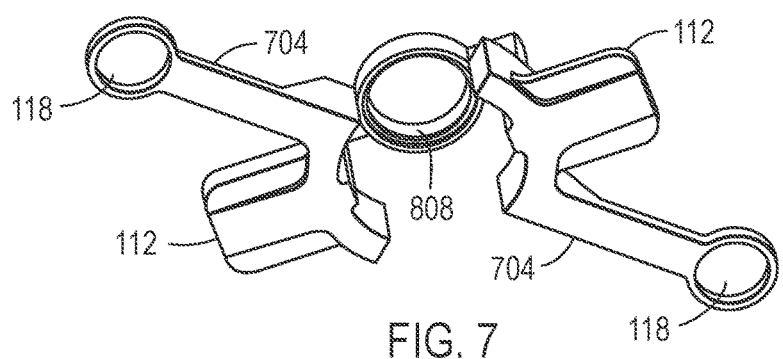
Figure 8:
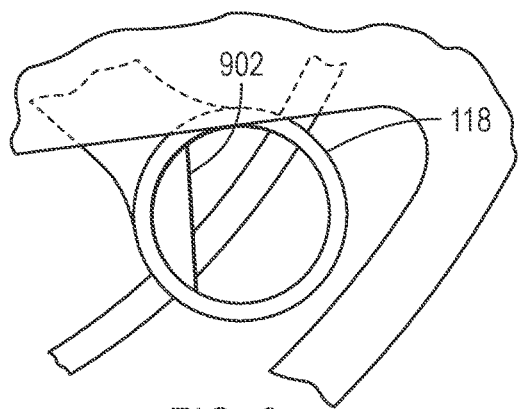

FIG. 6, FIG. 7, and FIG. 8 include illustrations of an exemplary stop plate 110. The stop plate 110 can engage a coupler 114 and a rotor plate 102 such that the stop plate 110 is rotatable relative to the rotor plate 102 and coupler 114 (illustrated in FIG. 1 and FIG. 2). The stop plate 110 includes wings 112 to engage buckets 104 when in a closed position. In a particular example, the wings 112 included a chamfered surface 702 that engages the buckets 104 when the stop plate 110 is closing and pushes the buckets into the closed position. The stop plate 110 can further include a central opening 808 to engage a central shaft of the coupler 114.

Further, the stop plate 110 includes arms 704 and distal rings 118. The rings 118 can be engaged to permit relative rotation of the stop plate 110 around the axis 116 relative to the coupler 114 and rotor plate 102 (illustrated in FIG. 1 and FIG. 2). Optionally, the stop plate 110 includes stop surfaces 710 that engage stop surfaces (e.g., stop surfaces 1004 of FIG. 9 and FIG. 10) of the coupler 114 when moved between the open and closed positions. Further, the stop plate 110 can include recesses 706 to receive magnets. The magnets can assist with securing the stop plate 110 to the coupler 114 and maintain the stop plate 110 in a position during spinning of the rotor assembly. In particular, the coupler 114 or the rotor plate 102 can include complementary magnets that provide an attractive force when the stop plate 110 is in the closed or open position. When the stop plate 110 is in the closed or open positions and the ring 118 of the stop plate 110 is not engaged, the stop plate 110 spins around the central axis with the rotor plate 102 and the coupler 114.

As illustrated in FIG. 8, the distal ring 118 can be partially filled with a chamfered slip 902. The chamfered slip 902 can be configured to allow a tip to hold the stop plate 110 while the rotor assembly rotates, bringing the stop plate to a 90° position relative to its starting position, moving the stop plate 110 from an open position to close position or vice versa.

Figure 9:
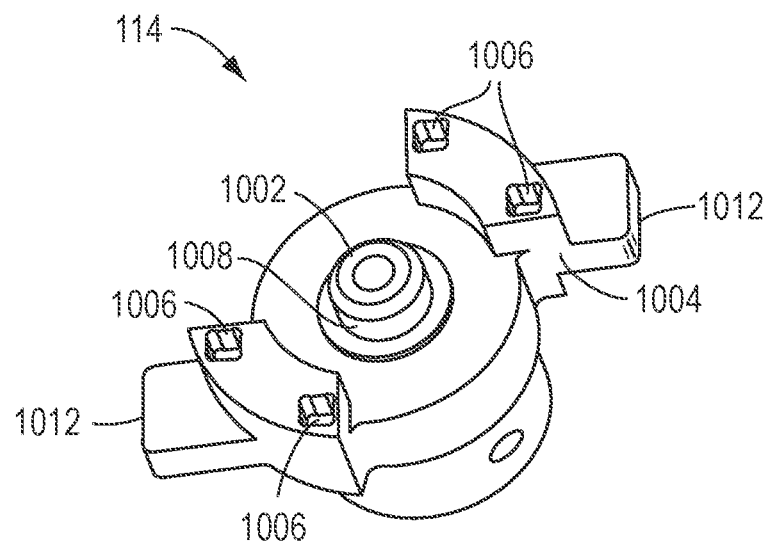
FIG. 9 and FIG. 10 include illustrations of an exemplary coupler.
Figure 10:
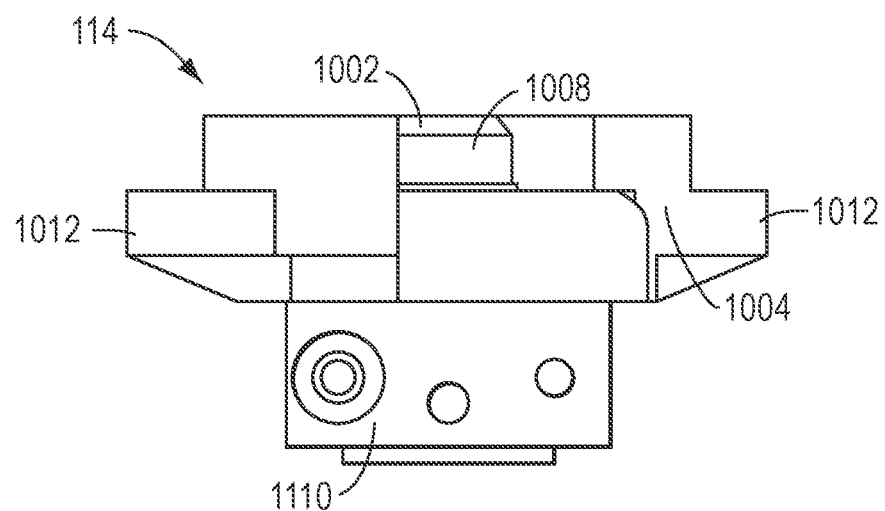

FIG. 9 and FIG. 10 include illustrations of an exemplary coupler 114. The coupler 114 can include wings 1012 to engage slots 308 of a rotor plate 102, as illustrated in FIG. 3. When engaged with the rotor plate 102, the wings 1012 limit the movement of the rotor plate 102 relative to the coupler 114. The coupler 114 can further include a central shaft chamfer 1002 for engaging a bearing of a rotor plate 102 and can include a contact surface 1008 for engaging a stop plate 110. When the stop plate 110 is rotated from an open to a closed position and back, the stop plate 110 can include a stop surface 710 that engages the stop surface 1004 of the coupler 114. In addition, the coupler 114 can include recesses 1006 to receive magnets that can secure the stop plate 110 in a desired position through attraction to magnets of the stop plate 110. As illustrated in FIG. 10, the coupler 114 can further include a motor shaft coupling 1110 to couple the coupler 114 and rotor assembly 100 to the motor shaft of a centrifuge motor.

Figure 11:
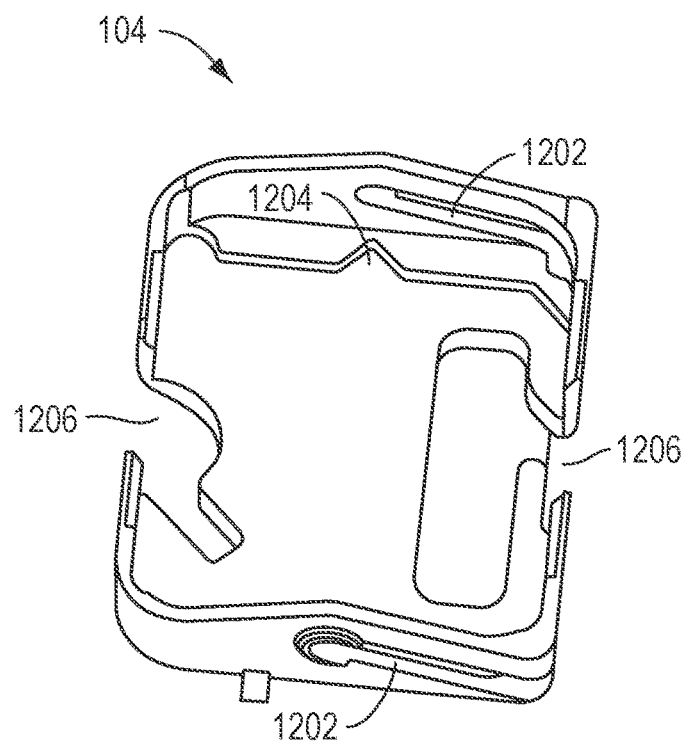
FIG. 11 and FIG. 12 include illustrations of an exemplary bucket.
Figure 12:
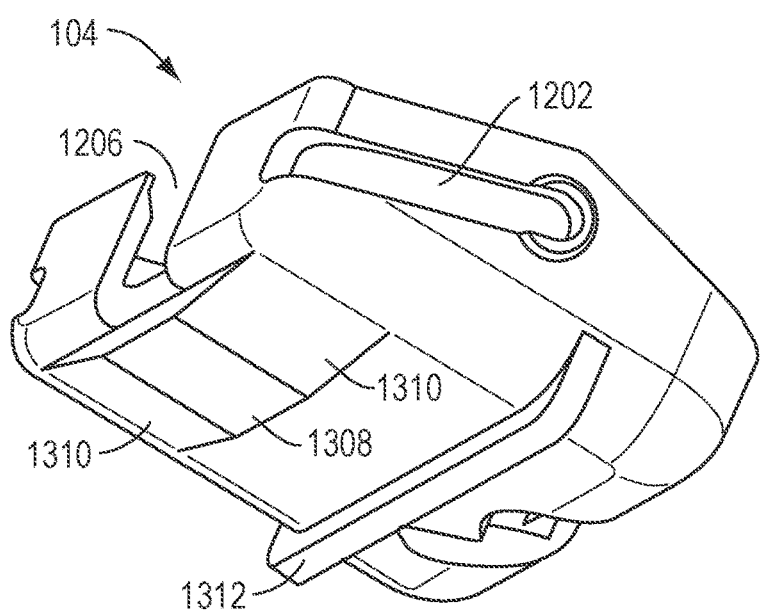

FIG. 11 and FIG. 12 include illustrations of an exemplary bucket 104. The exemplary bucket 104 includes channels 1202 to slidably engage axles 120 attached to a rotor plate 102. The bucket 104 can further include a patterned surface 1204 to engage a sensor array component. Openings 1206 can be provided to further secure the sensor array component or accommodate protruding edges of the sensor array component.

At a bottom surface of the bucket 104, as illustrated in FIG. 12, a stop surface 1308 can be positioned between chamfered surfaces 1310. When the stop plate 110 is moved into a closed position, the chamfered surface 702 of the wings 112 of the stop plate 110 engage the chamfered surface 1310 of the bucket 104, moving the bucket 104 into a position that secures the bucket 104 and limits rotation of the bucket 104. Further, the bucket 104 can include a rail or other feature 1312 that permits the bucket 104 to sit flat on a desktop surface when the bucket 104 is not engaged with the rotor assembly 100.

Figure 13:
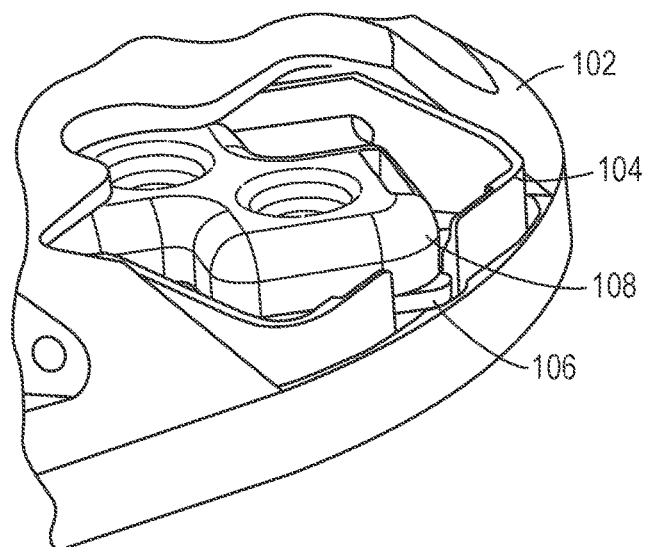
FIG. 13 and FIG. 14 include illustrations of a portion of an exemplary rotor assembly.
Figure 14:
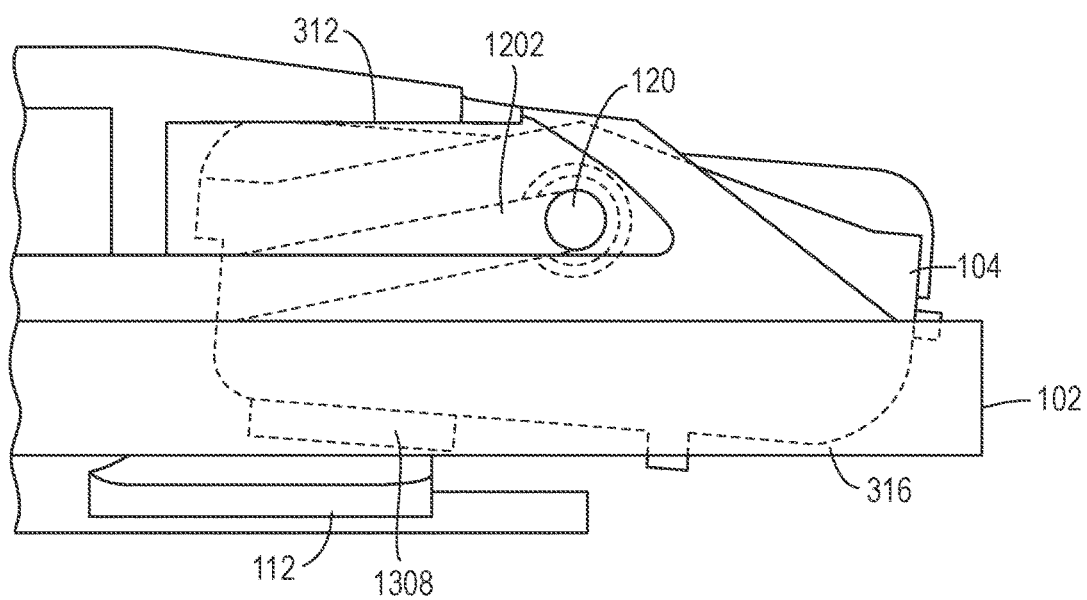

In particular, as illustrated in FIG. 13 and FIG. 14, the bucket 104 can be slid into position in the rotor plate 102, engaging axles 120 along channels 1202. When the sensor array component 106 including the cap 108 is inserted into the bucket 104 and the wing 112 of the stop plate 110 engages the stop surface 1308 of the bucket 104, the bucket 104 is secured against a top stop surface 312 or against a rear stop surface 316 of the rotor plate 102. As illustrated, the bucket 104 can have a horizontal or negative angle relative to the plane of rotation of the rotor assembly 100 when the stop plate is in the closed position. For example, the bucket 104 and associated sensor array component 106 can have an angle in a range of 5° to −15°, such as an angle of 5° to −10°, or even an angle of 0° to −5° relative to the plane of rotation of the rotor assembly when the stop plate is in the closed position. Herein, positive angles indicate that the top of the sensor array component 106 or bucket 104 tilt to face the central axis 116 of the rotor assembly. When the stop plate 110 is in the open position, the bucket 104 can swing around axles 120. In particular, when the rotor assembly 100 is rotating around the central axis 116, the bucket 104 may be weighted to have an angle of at least 45°, such as at least 75°, or even at least 80° during spinning of the rotor assembly 100. During spinning of the rotor assembly 100, the bucket 104 may swing to a position or angle in a range of 85° to 110°, such as an angle of 85° to 105°, or even an angle of 85° to 95°, such as approximately 90°, relative to the plane of rotation of the rotor assembly 100.

Figure 15:
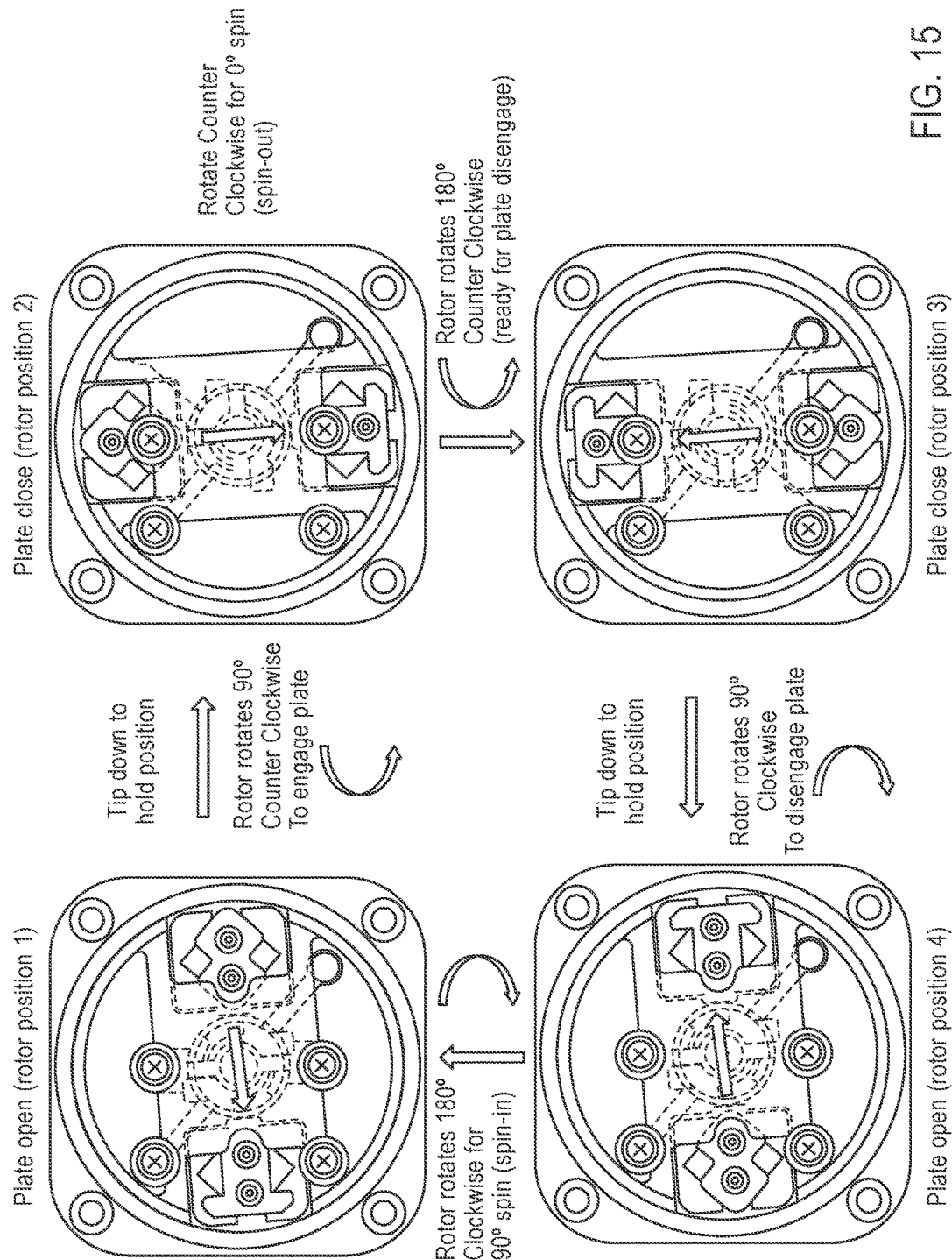
FIG. 15 includes an illustration of an exemplary rotor assembly.

To further illustrate the operation of the rotor assembly, FIG. 15 shows the rotor in an open position at rotor position 1. A tip can engage a ring of the stop plate, and the rotor plate can be rotated 90°, for example counterclockwise, to engage the rotor plate and buckets in the closed rotor position 2. To open the stop plate, the rotor assembly can be rotated 90° counter clockwise to rotor position 3. A tip can be applied into a ring of the stop plate, and the rotor plate can rotate 90° clockwise to disengage the stop plate and move into open rotor position 4. The rotor assembly can further be rotated 180° clockwise to begin the process of closing and opening the rotor assembly again.

Figure 16:
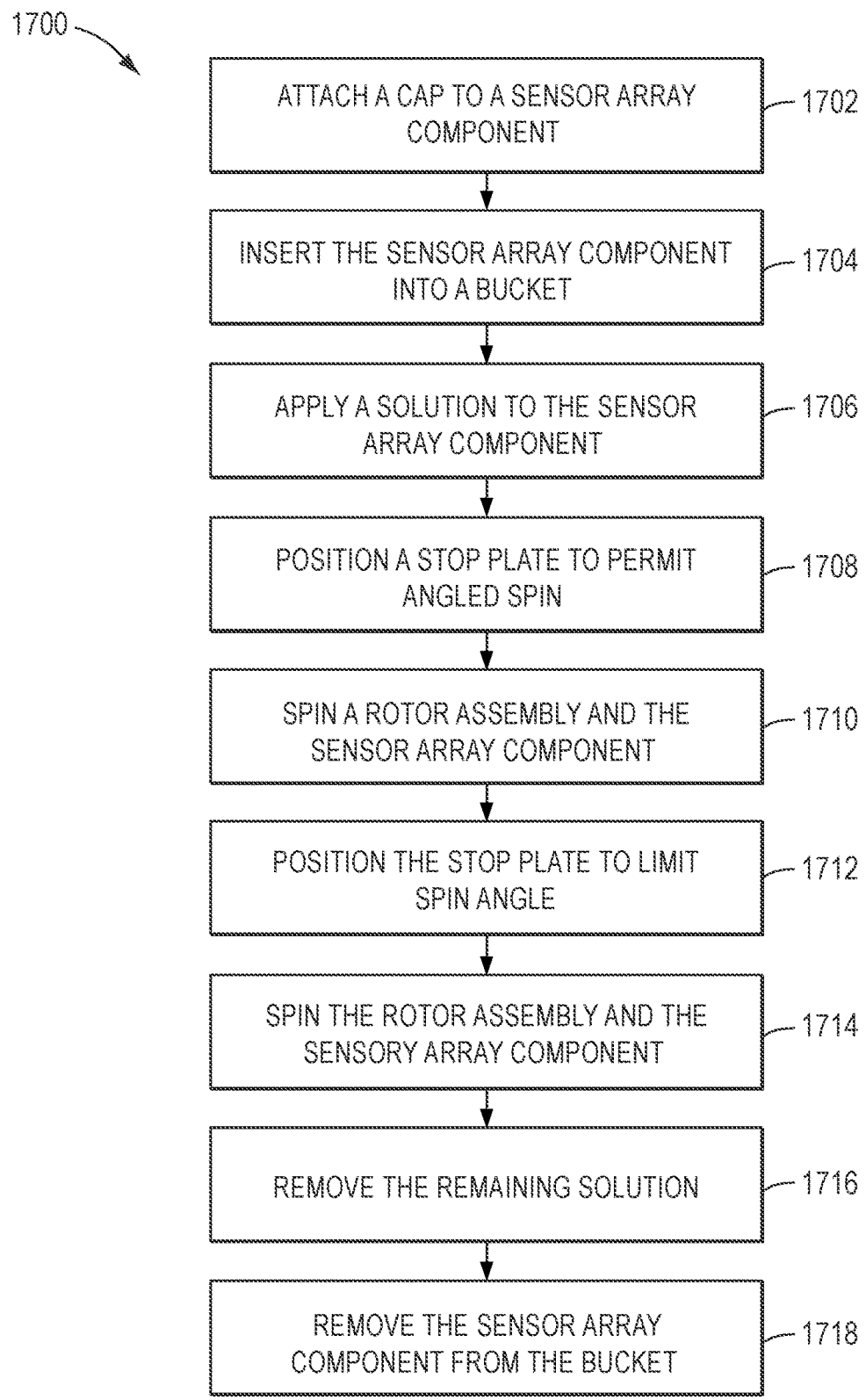
FIG. 16 and FIG. 17 include illustrations of block flow diagrams of exemplary methods for using a centrifuge including an exemplary rotor assembly.

In particular, the rotor assembly can be used to load samples onto a sensor array component. As illustrated in FIG. 16, a method 1700 optionally includes attaching a cap to a sensor array component, as illustrated at 1702. In particular, the cap can provide easier access for pipetting solutions into and out of the sensor array component.

The sensor array component is inserted into a bucket, as illustrated at 1704. In particular, the bucket secures the sensor array component when the rotor assembly spins.

Optionally, the bucket is inserted into the rotor assembly, and a solution is applied to the sensor array component, as illustrated at 1706. In particular, the solution can be applied while the stop plate is in the closed position to hold the bucket in place. Alternatively, the solution can be applied prior to inserting the bucket into the rotor plate.

As illustrated at 1708, the stop plate can be positioned to an open position that permits the bucket and sensor array component to swing relative to an axis extending in the direction of the rotation of the rotor assembly. In particular, the bucket can be weighted to rotate to a positive angle around an axis that extends in a direction along a direction of rotation of the rotor assembly.

Once the stop plate has been moved into an open position, the rotor assembly including the bucket and sensor array component can be spun, as illustrated at 1710. As a result, the bucket and sensor array component can rotate to an angle of at least 45°, such as at least 75°, or even at least 80° during spinning of the rotor assembly. During spinning of the rotor assembly, the bucket may swing to a position or angle in a range of 85° to 110°, such as an angle of 85° to 105°, or even an angle of 85° to 95°, such as approximately 90°, relative to the plane of rotation of the rotor assembly.

Following spinning, the stop plate can be positioned into a closed position to limit the spin angle of the bucket and sensor array component, as illustrated at 1712. For example, the stop plate can limit the spin angle of the bucket to near zero or slightly negative. Optionally, the rotary assembly and the sensor array component can be spun, as illustrated at 1714, while the stop plate is in the closed position and limits the movement of bucket. In particular, spinning at a negative angle can facilitate removal of solution from the sensor array component.

The remaining solution can be removed from the sensor array component, as illustrated at 1716, for example, by pipetting the remaining solution from a recess in the cap. The sensor array component can then be removed from the bucket as illustrated at 1718 and used in a separate testing apparatus.

Figure 17:
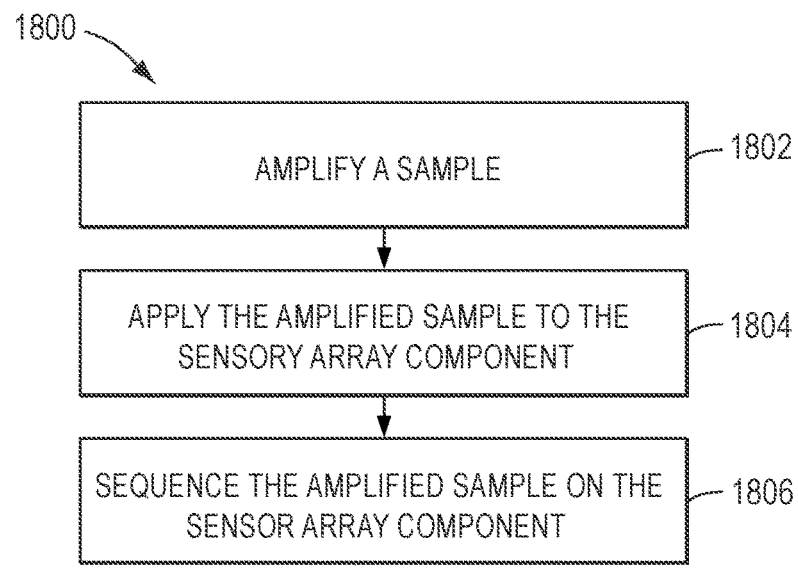

In a particular example, the sensor array component has particular use when sequencing target polynucleotides. As illustrated in the method 1800 of FIG. 17, a polynucleotide sample can be amplified, as illustrated at 1802. In particular, the sample can be amplified on bead or particulate substrates.

As illustrated at 1804, the amplified sample, particularly beads or particle substrates, can be applied to a sensor array component. In particular, a solution including the amplified sample is applied to or loaded into the sensor array component, and undergoes spinning under various angular conditions, securing to the bead or particulate substrates into the sensor array component. The sensor array component can then be inserted into a sequencing apparatus and the amplified sample that is loaded onto the sensor array component can be sequenced, as illustrated at 1806.

Figure 18:
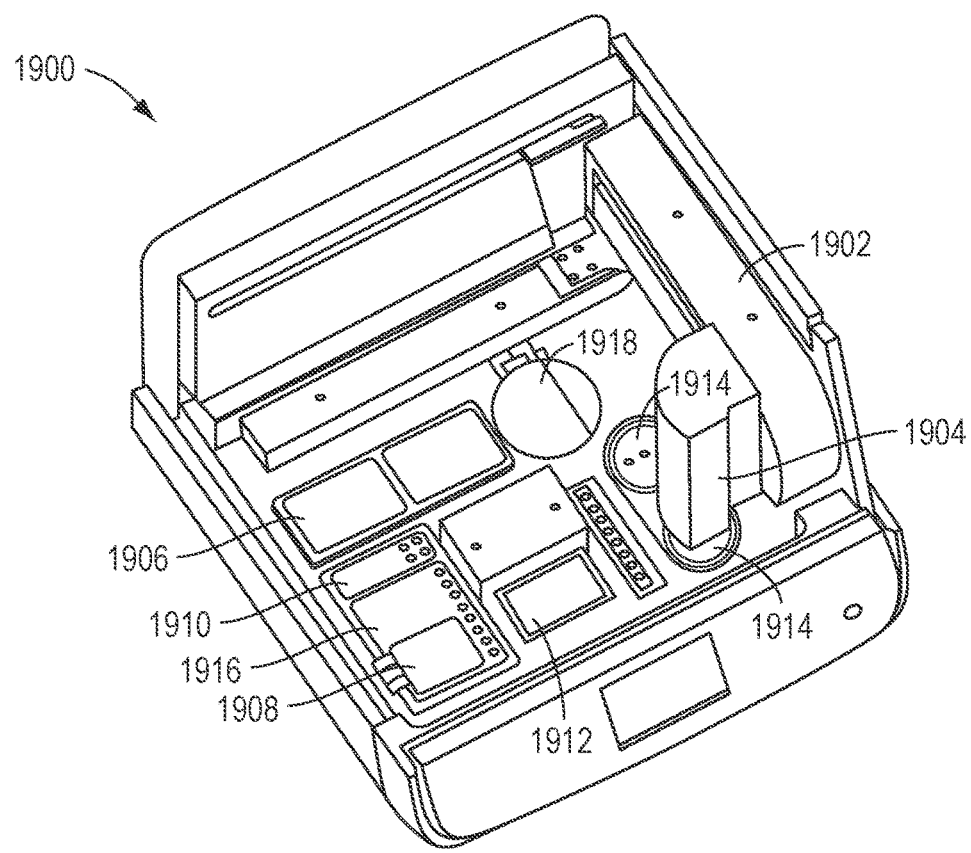
FIG. 18 includes an illustration of an exemplary pipetting robot.

Such a rotor assembly finds particular use in a pipetting robot assembly. FIG. 18 illustrates an exemplary configuration. The system 1900 includes a translation device, such as a xyz-robot 1902 operable to move a syringe pump 1904 over ranges of three orthogonal axes. The system 1900 further includes a tip rack 1906 for storing pipette tips useful by the syringe pump 1904. The system 1900 can also include a tube rack 1916 that can store empty tubes or can store strips of reagent tubes, such as reagent strip 1908. In a further example, the system 1900 can include a chilled block 1910 for storing temperature sensitive reagents, such as enzymes. The system 1900 can further include a thermocycler 1912, one or more emulsion breaking centrifuges 1914, and a bead loading centrifuge 1918 with motor. In particular, the bead loading centrifuge 1918 can include a rotor assembly, such as an embodiment of the rotor assembly described above. The system 1900 can further include an optical sensor or a tip removal device.

In operation, the translation device 1902 manipulates the position of the syringe pump 1904 to retrieve tips from the tip rack 1906 and perform the various functions of the system 1900. For example, the syringe pump 1904 can be utilized along with reagents of the reagent rack 1916 to form an emulsion including enzymes and a sample in an aqueous discontinuous phase surrounded by an immiscible continuous phase. For example, the sample and enzyme solutions can be stored in the chilled reagent block 1910. The emulsion can be formed within a tube in the reagent rack 1916. In particular, the emulsion can be generated by rapid pipetting. In another example, the emulsion can be generated by pipetting through a restriction.

Following formation of the emulsion, the emulsion can be transferred to a thermocycler plate on a thermocycler 1912 using the translation device 1902 and the syringe pump 1904. The thermocycler plate 1912 can be utilized to perform polymerase chain reaction (PCR) or recombinase polymerase amplification (RPA). Upon completion of the PCR reaction, the emulsion can be transferred from the thermocycler 1912 to one of the emulsion breaking centrifuges 1914. The emulsion can be injected into the emulsion breaking centrifuge 1914 that includes tubes having a surfactant solution. As the centrifuge rotates, the emulsion is injected into the centrifuge. When the emulsion contacts the surfactant solution within the tubes of the centrifuge 1914, aqueous phase components are driven into the solution while oil phase components are removed from the tube.

The PCR or RPA process can generate amplified beads including a number of target polynucleotides. Such amplified beads can be washed and separated from other aqueous solution components using an enrichment system. In particular, the reagent rack 1916 can be modified with the magnet system to permit enrichment using magnetic particles that bind to the amplified beads.

Following enrichment, the beads can be transferred and loaded onto a sequencing device, such as a chip configured for detecting sequencing byproducts, using the loading centrifuge 1918. For example, aliquots of the solution including the amplified beads can be injected into ports on the sequencing device disposed on the rack within the loading centrifuge 1918. The centrifuge 1918 can be positioned and spun, for example, as described above, to facilitate the loading. In particular, a tip attached to the syringe pump 1904 can be positioned in a ring of a stop plate to move the stop plate between open and closed positions. The process can be repeated one or more times to improve loading density. As a result, a sequencing device loaded with amplified particles, incorporating amplified target nucleotides from the sample, is provided with minimal human interaction.

Throughout the process, the syringe pump 1914 can utilize a variety of pipette tips acquired from the pipette tip rack 1906. Further, tips can be provided that assist with movement of magnets, loading of tubes within the emulsion breaking centrifuge 1914, configuring the loading centrifuge, or other functions. To assist with removal of the tips from the syringe pump 1904, a tip removal device can be provided.

In other embodiments, the stop plate can be formed from two separate components, the magnets can be positioned at different locations on different components, and the axles of the buckets can be secured to the buckets and be of different sizes in contrast to securing the axles to the rotor plate. While exemplary embodiments are illustrated in FIG. 19-FIG. 26, the illustrated features can be interchangeable between embodiments.

Figure 19:
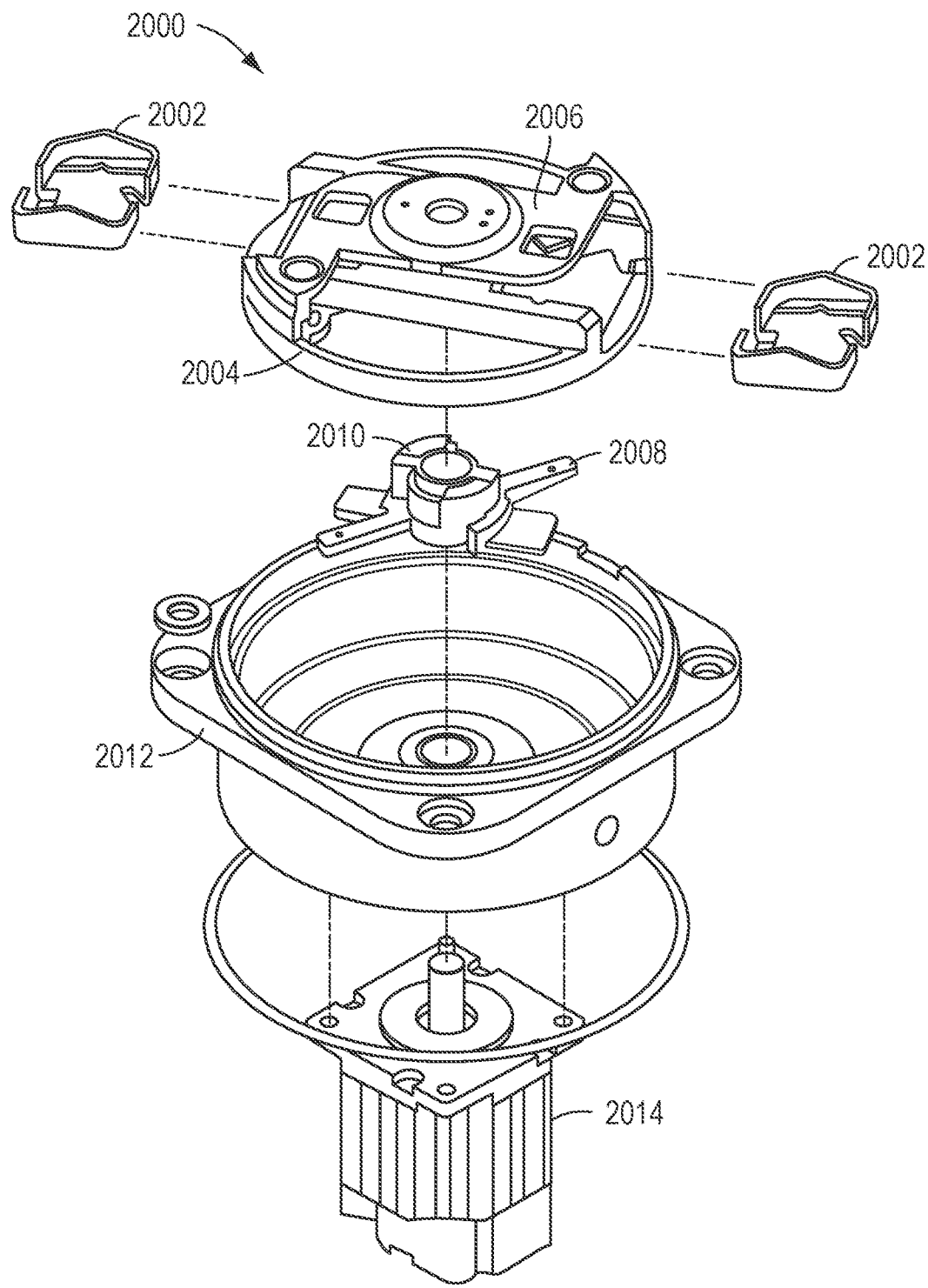
FIG. 19 includes an illustration of a centrifuge assembly.

As illustrated in FIG. 19, a centrifuge 2000 includes a bucket 2002 that can be secured in a rotor plate 2004. An upper stop plate 2006 is positioned coaxially with the rotor plate 2004. The upper stop plate 2006 can be coupled to a lower stop plate 2008, which includes wings to engage the buckets 2002. The rotor plate 2004 is secured to a coupler 2010, which secures the rotor assembly to the shaft of a motor 2014. The upper stop plate 2006 and the lower stop plate 2008 can be rotatably secured to the coupler 2010. The rotor assembly can fit inside a casing 2012.

Figure 20:
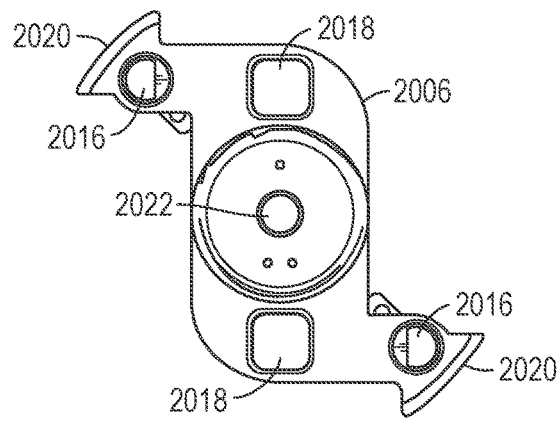
FIG. 20, FIG. 21, and FIG. 22 include illustrations of exemplary upper stop plates.
Figure 21:
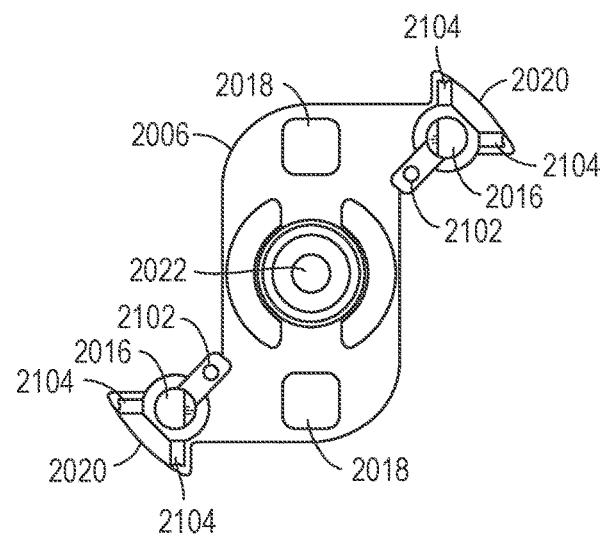
Figure 22:
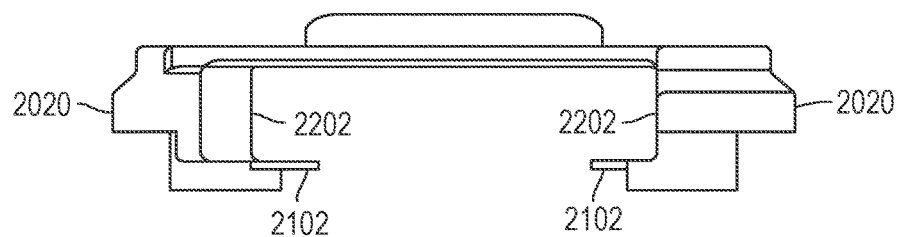

FIG. 20, FIG. 21, and FIG. 22 includes illustrations of an upper stop plate 2006. Similar to the stop plate described above, the upper stop plate 2006 includes openings 2016 to engage a robot, in particular a pipetting robot, and allow rotation of the upper and lower stop plates relative to the rotor plate 2004. In addition, the upper stop plate 2006 can include a window 2018 that provides access to ports on devices within the buckets 2002, for example, when the upper stop plate 2006 and lower stop plate 2008 are engaged with the bucket 2002. The upper stop plate 2006 can also include a central bore 2022 to engage the coupler 2010. Edges of the upper stop plate 2006 can be configured with surfaces 2020 that correspond with an inner surface of a casing 2012.

As illustrated in the bottom view of the upper stop plate 2006 in FIG. 21, the upper stop plate 2006 can include a coupling arm 2102 to secure the upper stop plate 2006 to the lower stop plate 2008. The upper stop plate 2006 can also include magnets 2104 to engage magnets on the rotor plate 2004 to assist with holding the position of the upper stop plate 2006 and lower stop plate 2008 in the designated position. Alternatively, magnets can be positions on the lower stop plate 2008.

As illustrated in the side view in FIG. 22, the upper stop plate 2006 can include extensions 2202 terminating in the coupling structures 2102 to engage the lower stop plate 2008. Alternatively, the lower stop plate 2008 can include the extension and coupling structure to engage the upper stop plate 2006. Using such a configuration, the upper stop plate 2006 can reside above the rotor plate 2004, and the lower stop plate 2008 can reside below the rotor plate 2004 relative to the axis of rotation of the rotor assembly.

Figure 23:
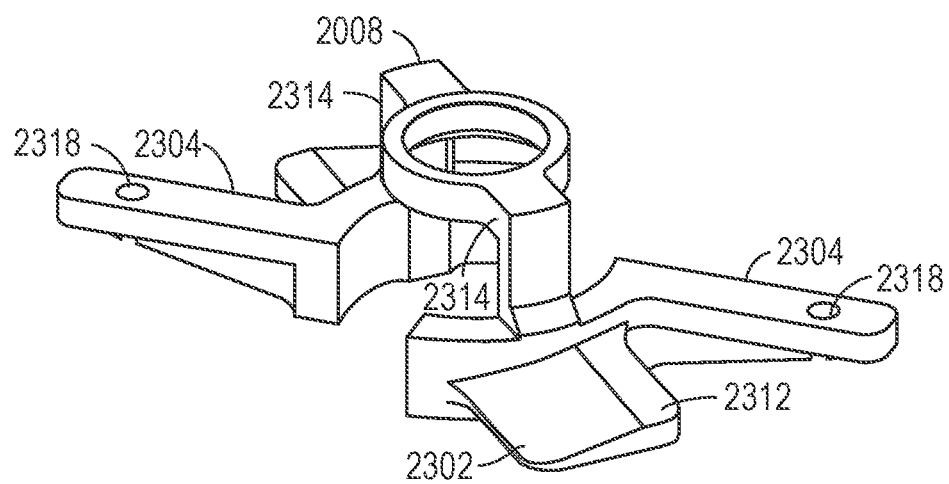
FIG. 23 includes an illustration of an exemplary lower stop plate.

FIG. 23 includes an illustration of the lower stop plate 2008. The lower stop plate includes wings 2302 to engage buckets 2002 disposed on the rotor plate 2004. The wings 2302 can include a horizontal planar surface 2312 that engages the buckets 2002 in a closed position, securing the buckets preventing their rotation. The lower stop plate 2008 can also include arms 2304 and coupling positions 2318 to engage the upper stop plate 2006. The lower stop plate 2008 can further include stop surfaces 2314 to engage stop surfaces on the coupler 2010.

Figure 24:
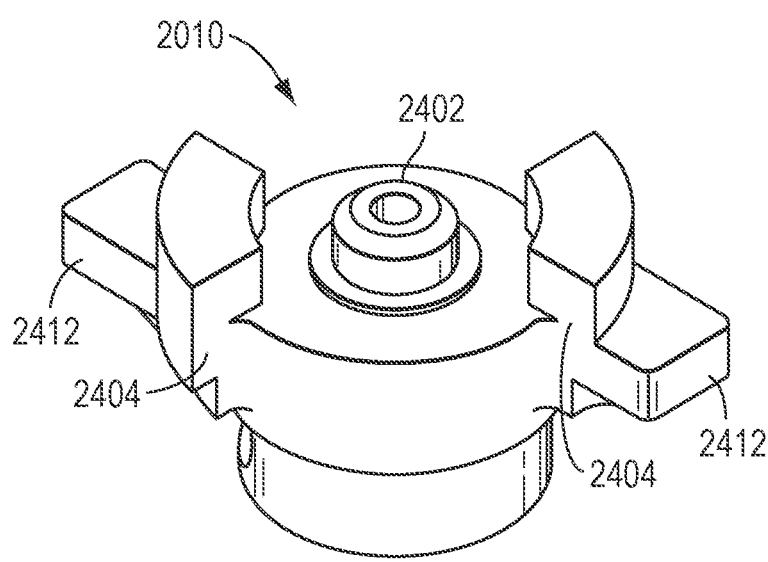
FIG. 24 includes an illustration of an exemplary coupler.
Figure 25:
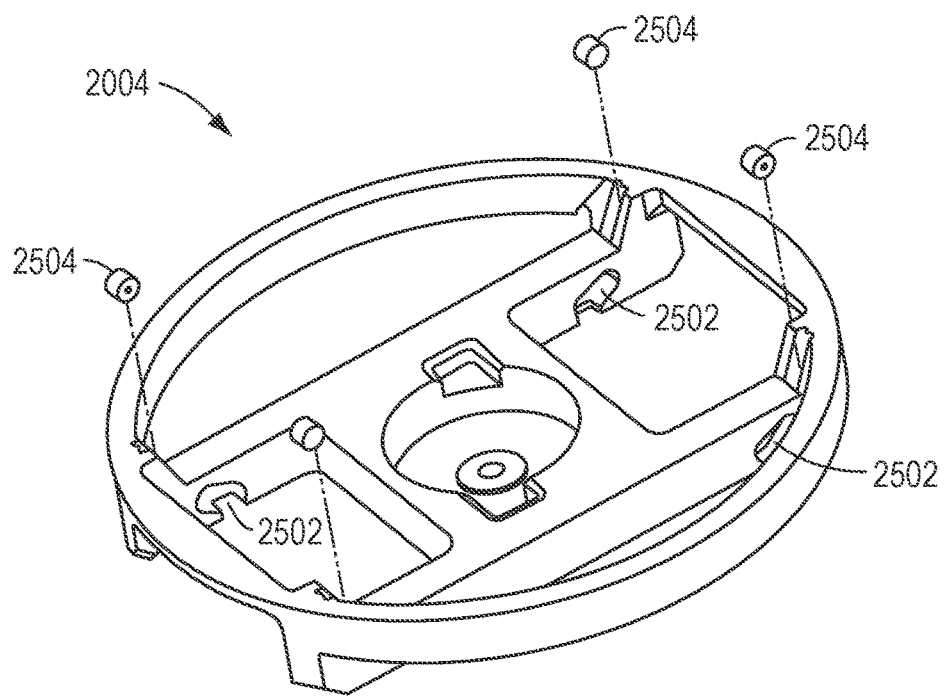
FIG. 25 includes an illustration of an exemplary rotor plate.

FIG. 24 illustrates a further exemplary embodiment of a coupler 2010. The coupler 2010 includes wings 2412 to engage the rotor plate 2004. In addition, the coupler 2010 includes a central shaft 2402 to engage the lower stop plate 2008, the rotor plate 2004, or the upper stop plate 2006. The upper stop plate 2006 and the lower stop plate 2008 engage the coupler 2010 in a manner that permits rotation relative to the coupler 2010. In particular, the upper stop plate 2006 or the lower stop plate 2008 when engaged to each other function similar to the stop plate described above and can moved between first and second positions, such as closed and open positions. The coupler 2010 includes stop surfaces 2404 that engage the stop surfaces 2314 of the lower stop plate 2008 when in one of the two positions.

The rotor plate 2004 includes features similar to those described in relation to the rotor plate above. In the example illustrated in FIG. 25, the rotor plate includes embedded magnets 2504 that can engage magnets embedded within the upper stop plate 2006. In particular, the stop plate 2006 or 2008 can be held in an open or closed position through the interaction of the magnets when the rotor assembly is rotating about a central axis of the motor 2014.

Figure 26:
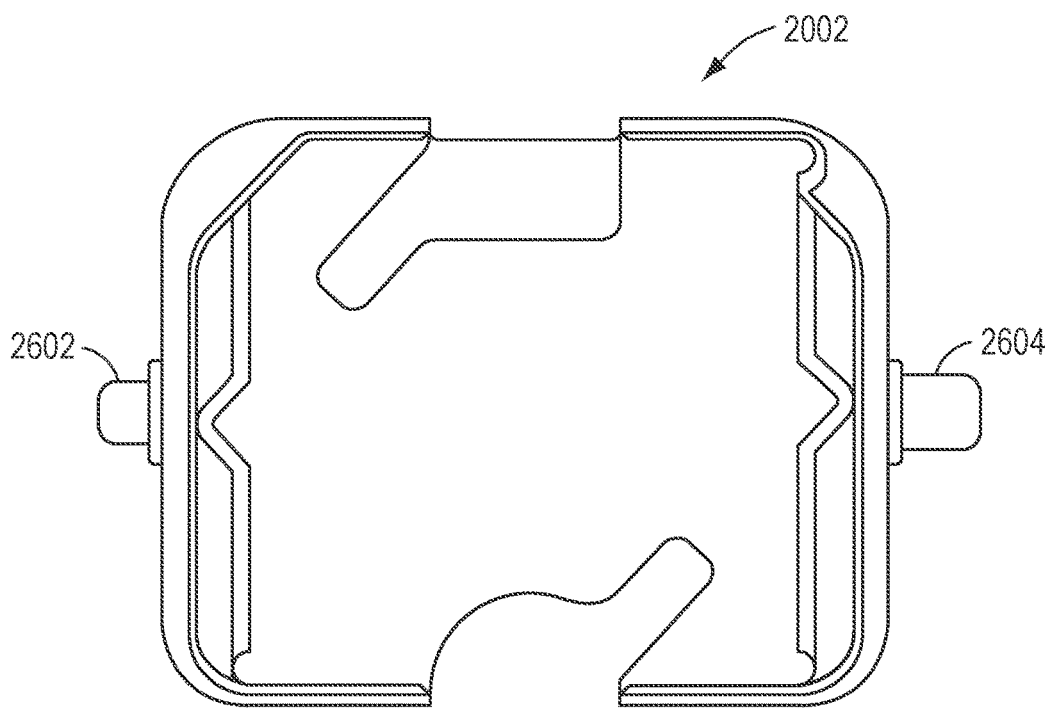
FIG. 26 includes an illustration of an exemplary bucket.

In further example, the rotor plate 2004 can include slots 2502 to receive axles of the buckets 2002. In such an example, the axles are secured to the buckets 2002 and can be slid into the slots 2502 to rotatably couple the buckets 2002 to the rotor plate 2004. In a particular example, the slots 2502 of the rotor plate 2004 can be configured to receive axles of different size. In particular, a slot 2502 on a clockwise side of the recess to receive the buckets 2002 can have a size different from the slots on the counterclockwise side. As illustrated in FIG. 26, the buckets 2002 can be configured with axles 2602 and 2604 of different diameter or different shape. As such, the buckets can engage the rotor plate 2004 in a single manner, preventing incorrect engagement of the buckets 2002 with the rotor plate 2004.

Figure 27:
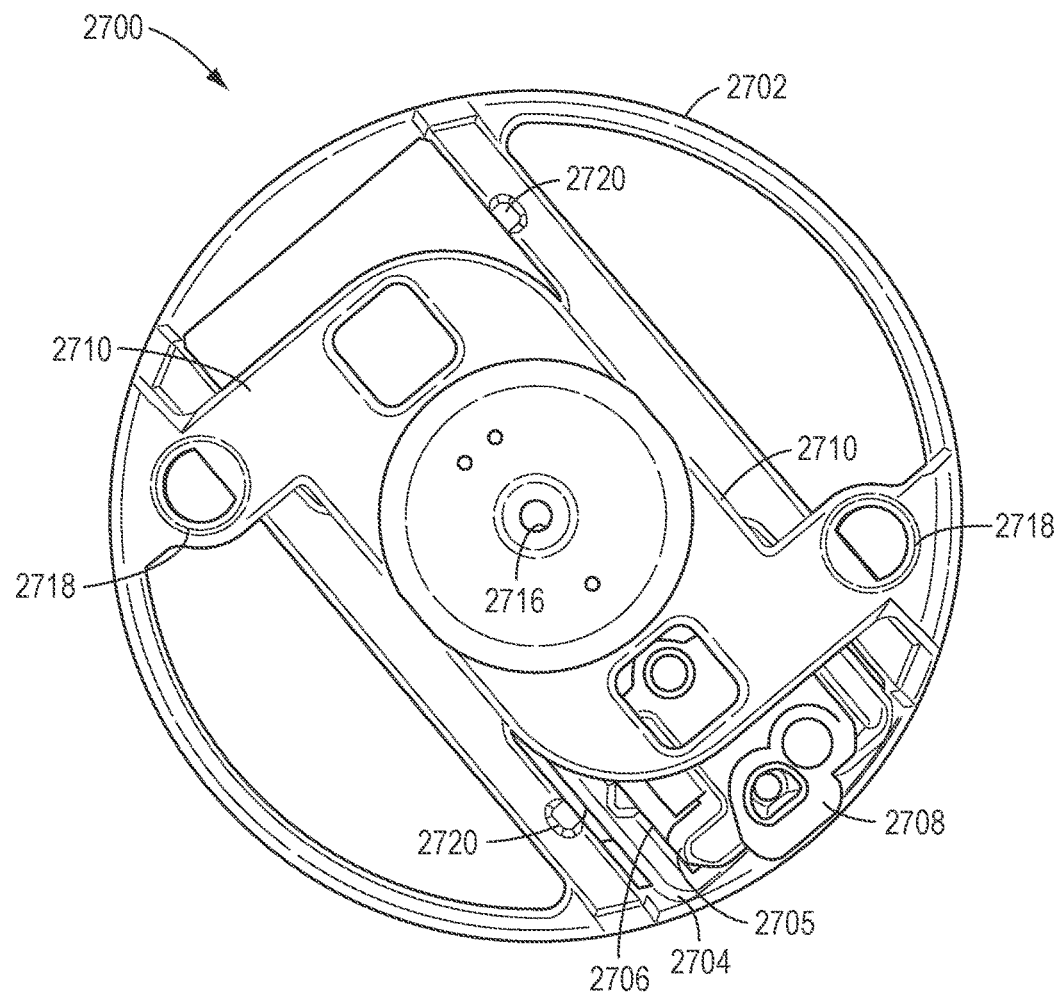
FIG. 27 includes an illustration of an exemplary rotor assembly.

In another exemplary embodiment illustrated in FIG. 27, a rotor assembly 2700 can rotate or spin around a central axis 2716. In an example, the rotor assembly 2700 can includes a rotor plate 2702, which engages axles 2720 of one or more buckets 2704. In the illustrated example, the rotor plate 2702 is configured to receive two buckets 2704. Alternatively, the rotor assembly and rotor plate 2702 can be configured to receive at least one bucket, such as at least two buckets, at least four buckets, or at least six buckets, but generally not greater than 20 buckets. The buckets 2704 are configured to receive a sensor array component 2706, a housing 2705 for the sensor array component 2706, and an associated cap 2708 for the housing 2705. The cap 2708 can assist with supplying a solution to or retrieving a solution from the sensor array component 2706.

Figure 28:
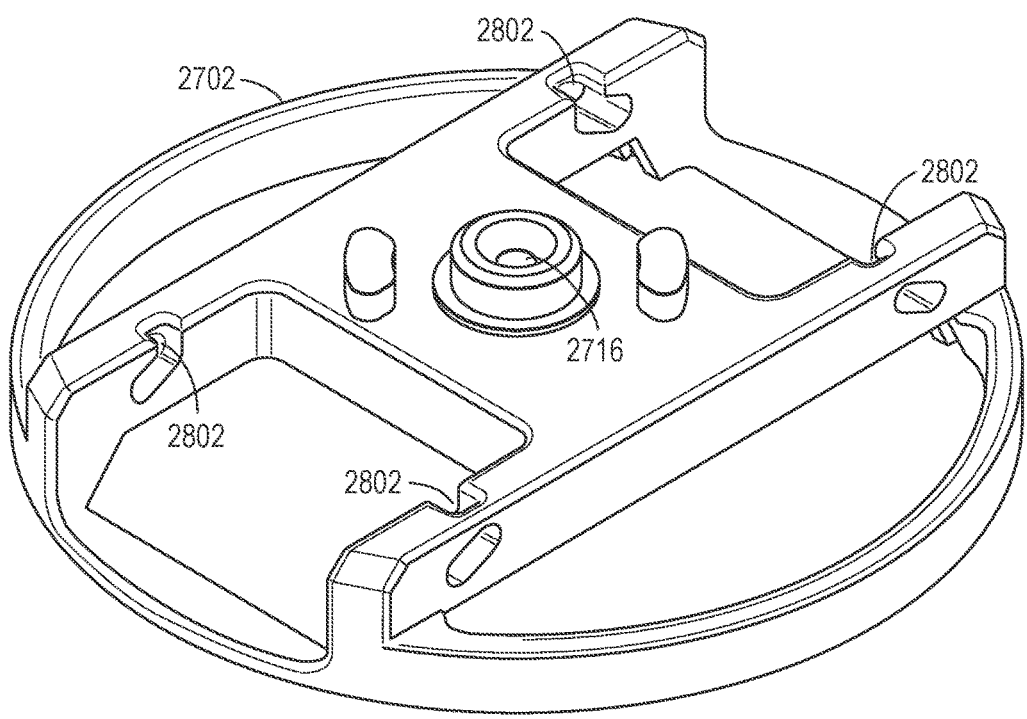
FIG. 28 includes an illustration of an exemplary rotor plate.

The rotor assembly 2700 can further include a stop plate 2710. The stop plate 2710 engages the buckets 2704, limiting rotation of the buckets 2704 around axles 2720. The stop plate 2710 can further include rings 2718 that can be engaged, for example, by a tip of a pipetting robot. Using a pipetting robot and optionally the associated centrifuge motor, the stop plate 2710 can be rotated around the central axis 2716 or relative to the rotor plate 2702, moving the stop plate 2710 from a closed position as illustrated in FIG. 1 to a 90° offset open position (shown in FIG. 32) in which the buckets 2704 are free to rotate around the axles 2720. As shown in FIG. 28, rotor plate 2702 includes channels 2802 that engage axles 2720.

Figure 29:
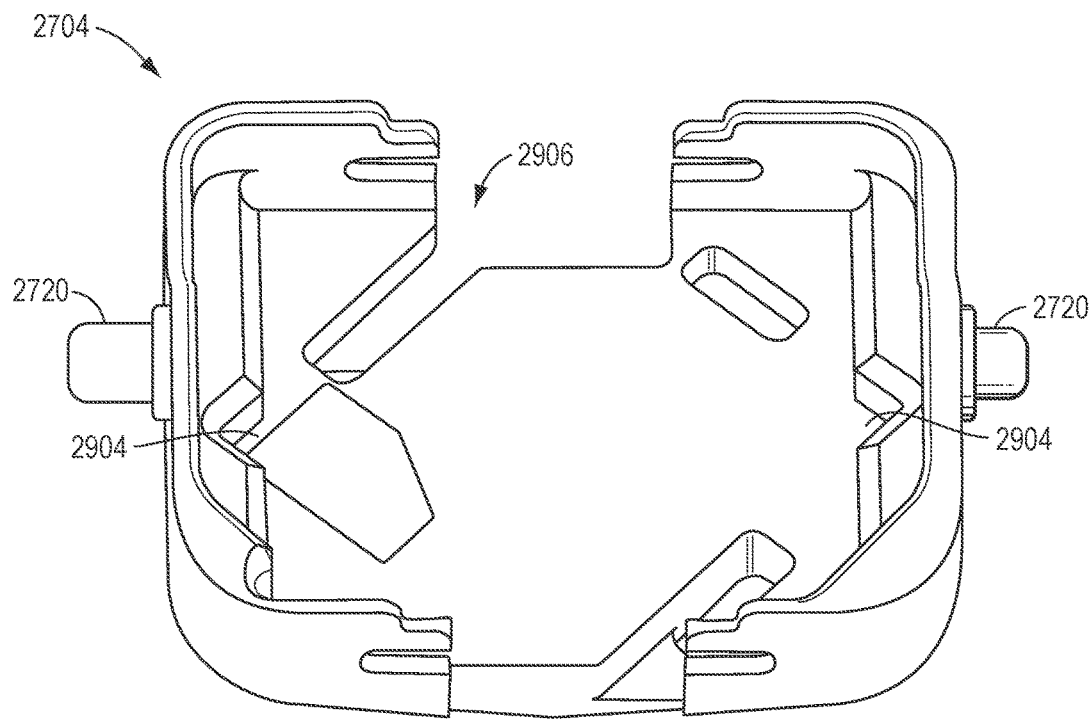
FIG. 29 includes an illustration of an exemplary bucket.

FIG. 29 illustrates an exemplary bucket 2704. The exemplary bucket 2704 includes axles 2720 to attach to a rotor plate 2702. The bucket 2704 can further include patterned surfaces 2904 to engage a sensor array component. Openings 2906 can be provided to further secure the sensor array component or accommodate protruding edges of the sensor array component.

Figure 30:
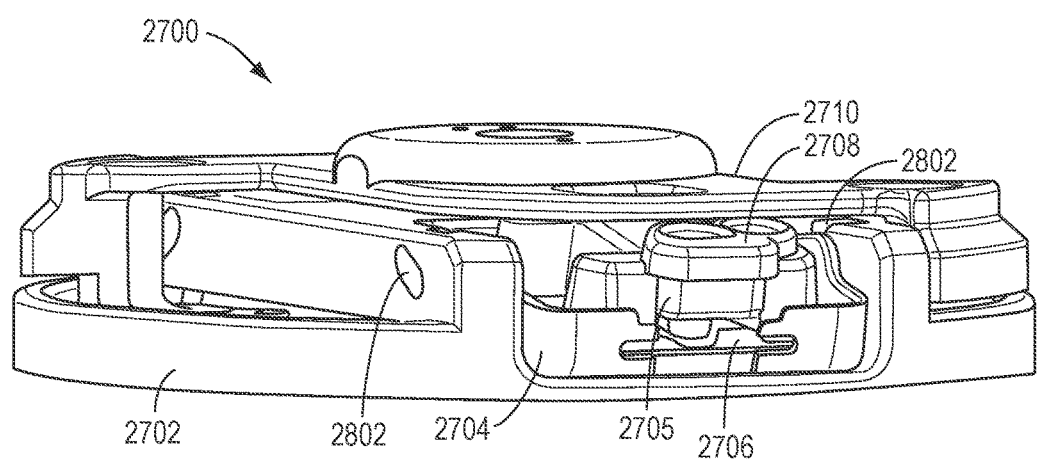
FIG. 30 includes an illustration of an exemplary rotor assembly.

In particular, as illustrated in FIG. 30, the bucket 2704 can be slid into position in the rotor plate 2702, engaging axles 2720 along channels 2802. When the sensor array component 2706 including the housing 2705 and the cap 2708 is inserted into the bucket 2704 and the stop plate 2710 engages the bucket 2704, the bucket 2704 is secured against the rotor plate 2702. As illustrated, the bucket 2704 can have a horizontal or negative angle relative to the plane of rotation of the rotor assembly 2700 when the stop plate 2710 is in the closed position. For example, the bucket 2704 and associated sensor array component 2706 can have an angle in a range of 5° to −15°, such as an angle of 5° to −10°, or even an angle of 0° to −5° relative to the plane of rotation of the rotor assembly 2700 when the stop plate 2710 is in the closed position. Herein, positive angles indicate that the top of the sensor array component 2706 or bucket 2704 tilts to face the central axis 2716 of the rotor assembly. When the stop plate 2710 is in the open position, the bucket 2704 can swing around axles 2720. In particular, when the rotor assembly 2700 is rotating around the central axis 2716, the bucket 2704 may be weighted to have an angle of at least 45°, such as at least 75°, or even at least 80° during spinning of the rotor assembly 2700. During spinning of the rotor assembly 2700, the bucket 2704 may swing to a position or angle in a range of 85° to 110°, such as an angle of 85° to 105°, or even an angle of 85° to 95°, such as approximately 90°, relative to the plane of rotation of the rotor assembly 2700.

Figure 31:
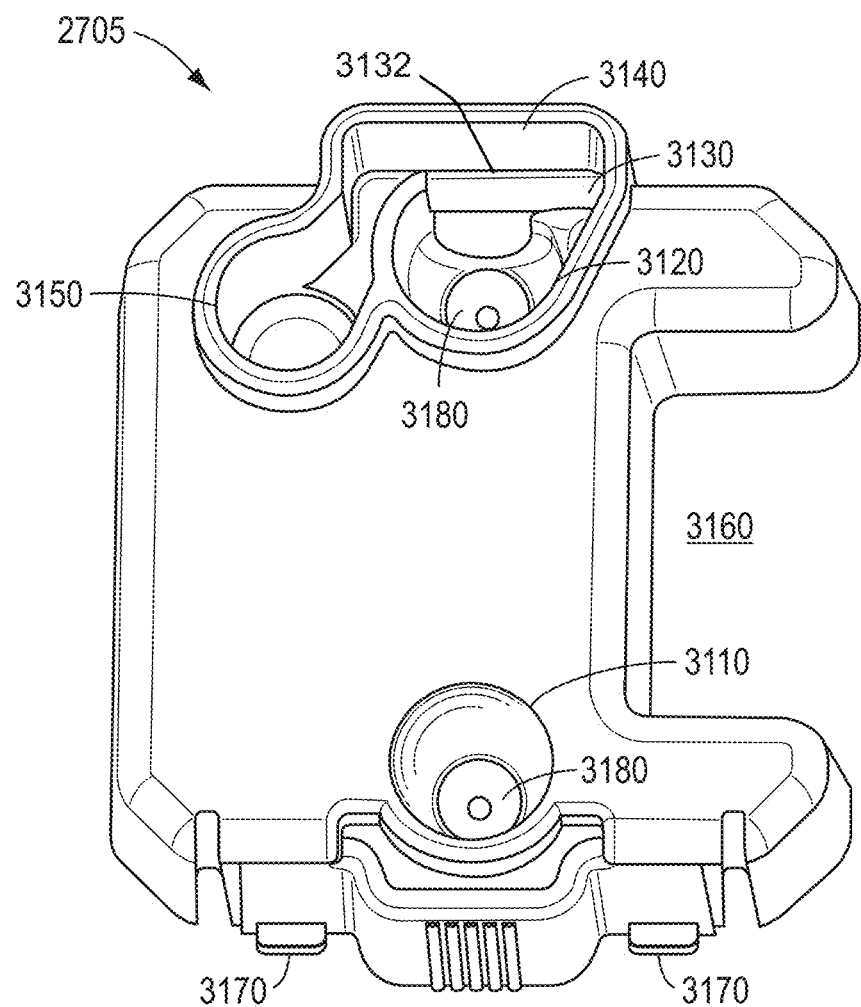
FIG. 31 includes an illustration of an exemplary housing.
Figure 32:
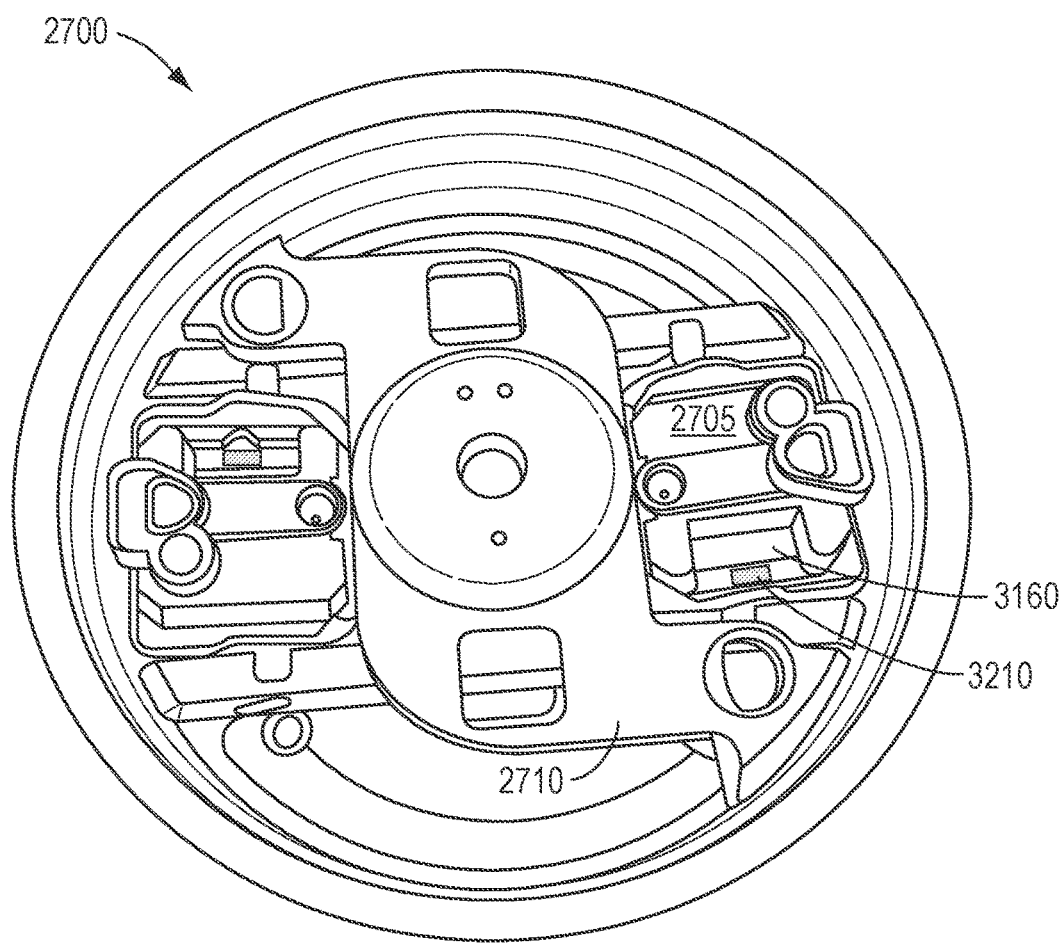
FIG. 32 includes an illustration of an exemplary rotor assembly.

As shown in FIG. 31, the housing 2705 includes a solution inlet 3110, to where solution is pipetted by, for example, a pipetting robot described above. In an example, the solution inlet 3110 is conical and can receive a pipette tip. For example, guiding the pipette tip into fluid communication with an inlet of a sensor array flow cell. When the rotor assembly 2700 is spun with the bucket 2704 in the orientation shown in FIG. 30 with a horizontal or negative angle relative to the plane of rotation of the rotor assembly 2700, the solution flows across the sensor array component 2706 (shown in FIG. 30), emerges from the solution outlet 3120, and is propelled due to centrifugal force over the solution retainer 3130 into the transfer basin 3140. In an example, the solution outlet 3120 is conical and can receive a pipette tip. Then, when the stop plate 2710 is in the open position (as shown in FIG. 32), and the rotor assembly 2700 is spun with the bucket 2704 in the orientation having a positive angle relative to the plane of rotation of the rotor assembly 2700, the solution flows from the transfer basin 3140 into the collection reservoir 3150.

When the housing 2705 is horizontal and viewed from a side, a lower surface or bottom of the transfer basin 3140 is higher than the lower surface or bottom of the collection reservoir 3150. In addition, when place in the rotor, the transfer basin 3140 is closer to a back edge of the housing 2705 than the collection reservoir 3150 or is disposed radially outwardly from the collection reservoir 3150. Further, the transfer basin 3140 is closer to a back edge of the housing 2705 than the solution outlet 3120 or is disposed radially outwardly from the solution outlet 3120. In an example, the collection reservoir 3150 has a conical shape to allow a pipette to draw fluid from the collection reservoir 3150 with limited fluid retention in the collection reservoir 3150.

The solution retainer 3130 is disposed between the solution outlet 3120 and the transfer basin 3140. The solution retainer 3130 can include an upper lip 3132 separating the transfer basin 3140 from the solution outlet 3120. The lower surface or bottom of the transfer basin 3140 can be lower than the lip 3132 of the solution retainer 3130.

The housing 3705 can also include clips 3170 to secure a sensor array and flow cell to a bucket. In an example, the clips 3170 can engage the sensor array and flow cell on one side and engage openings in the bucket on an opposite side.

In a further example, the housing 3705 can include gaskets 3180 to engage ports of a flow cell over a sensor array. In an example, the gaskets 3180 can be co-molded to the housing body and formed of a flexible polymeric material.

As also shown in FIG. 31, the housing 2705 can optionally include a slot 3160, so that, as shown in FIG. 32, a QR code 3210 on the sensor array component 2706 will be readable from above the rotor assembly 2700.

Figure 33:
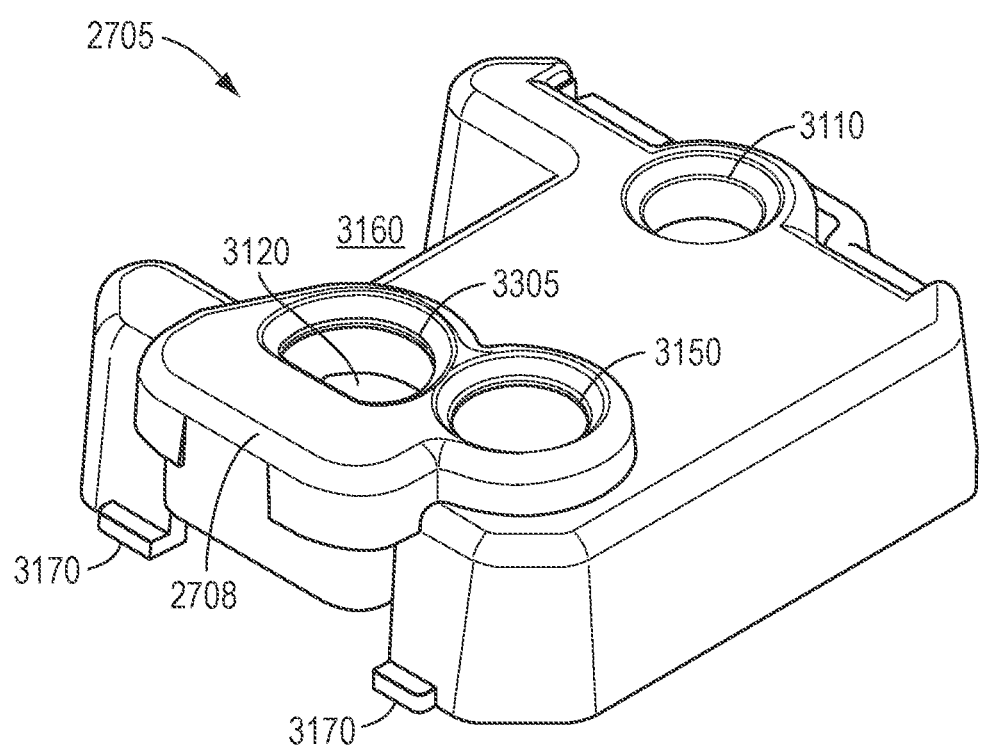
FIG. 33 includes an illustration of an exemplary housing.

As shown in FIG. 33, the housing 2705 can optionally include an opening 3305 over the solution outlet 3120. In an example, the cap 2708 prevents access to the transfer basin 3140 from a top of the housing 2705. The cap 2708 can define one or more openings. For example, the cap 2708 can define an opening for accessing the collection reservoir 3150 from a top of the housing 2705. In another example, the cap 2708 can define an opening 3305 for accessing the solution outlet 3120. The cap 2708 can define a fluid path between the cap 2708 and the lip of the solution retainer 3130, allowing fluid to flow from the solution outlet 3120 to the transfer basin 3140.

Figure 34:
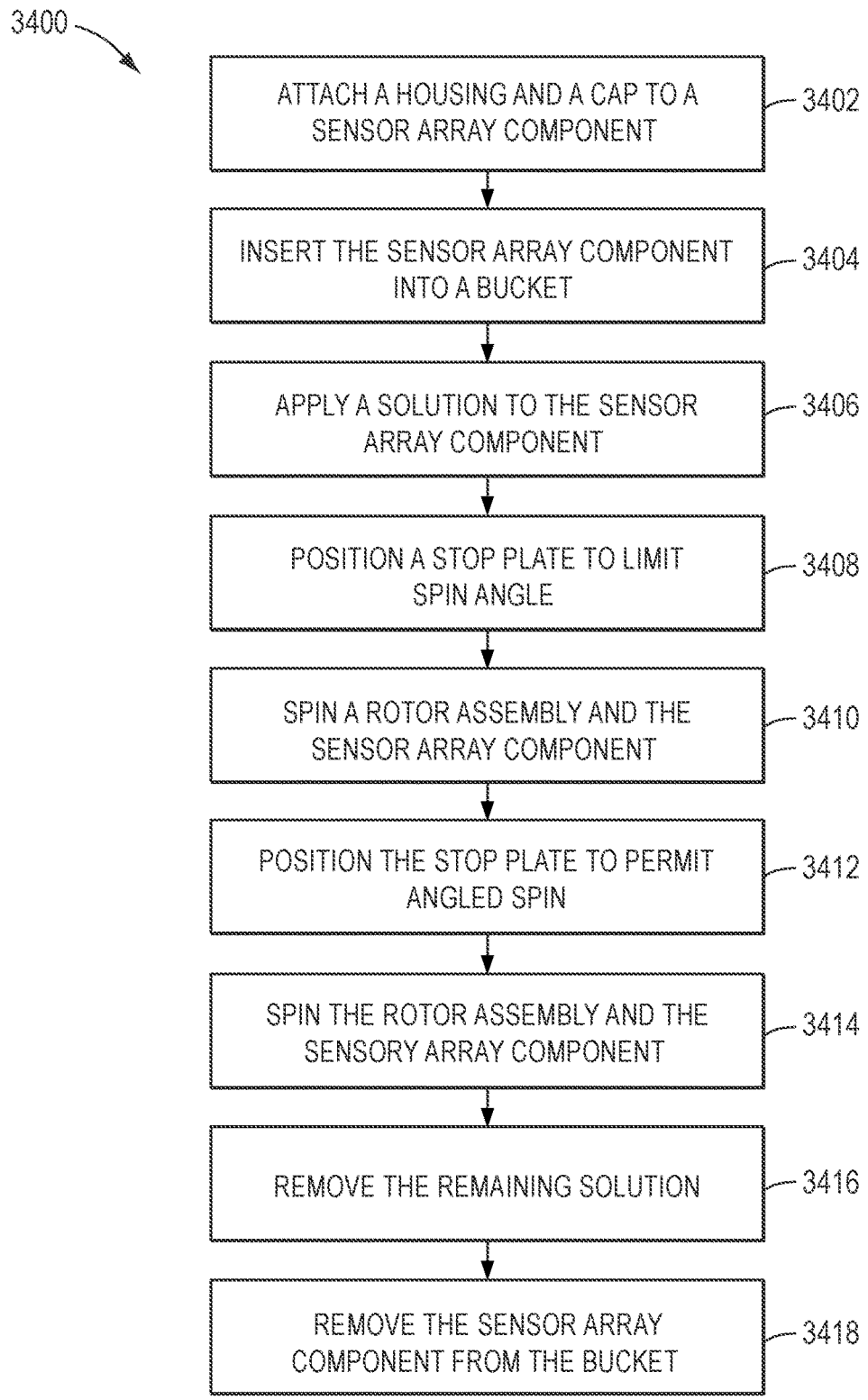
FIG. 34 includes an illustration of a block flow diagram of an exemplary method for using a centrifuge including an exemplary rotor assembly.

In particular, the rotor assembly can be used to load samples onto a sensor array component. As illustrated in FIG. 34, a method 3400 includes attaching a housing and, optionally, a cap to a sensor array component, as illustrated at 3402. In particular, the cap can provide easier access for pipetting solutions into and out of the sensor array component.

The sensor array component is inserted into a bucket, as illustrated at 3404. In particular, the bucket secures the sensor array component when the rotor assembly spins.

Optionally, the bucket is inserted into the rotor assembly, and a solution is applied to the sensor array component, as illustrated at 3406. In particular, the solution can be applied while the stop plate is in the closed position to hold the bucket in place. Alternatively, the solution can be applied prior to inserting the bucket into the rotor plate.

The stop plate can be positioned into a closed position to limit the spin angle of the bucket and sensor array component, as illustrated at 3408. For example, the stop plate can limit the spin angle of the bucket to near zero or slightly negative. The rotary assembly and the sensor array component can be spun, as illustrated at 3410, while the stop plate is in the closed position and limits the movement of bucket. In particular, spinning at a negative angle can facilitate flowing the solution over the solution retainer and into the transfer basin of the housing.

As illustrated at 3412, the stop plate can be positioned to an open position that permits the bucket and sensor array component to swing relative to an axis extending in the direction of the rotation of the rotor assembly. In particular, the bucket can be weighted to rotate to a positive angle around an axis that extends in a direction along a direction of rotation of the rotor assembly.

Once the stop plate has been moved into an open position, the rotor assembly including the bucket and sensor array component can be spun, as illustrated at 3414. As a result, the bucket and sensor array component can rotate to an angle of at least 45°, such as at least 75°, or even at least 80° during spinning of the rotor assembly. During spinning of the rotor assembly, the bucket may swing to a position or angle in a range of 85° to 110°, such as an angle of 85° to 105°, or even an angle of 85° to 95°, such as approximately 90°, relative to the plane of rotation of the rotor assembly, and the solution can flow from the transfer basin into the collection reservoir.

The remaining solution can be removed from the sensor array component, as illustrated at 3416, for example, by pipetting the remaining solution from the collection reservoir. The sensor array component can then be removed from the bucket, as illustrated at 3418, and used in a separate testing apparatus.

In an alternative example, the stop plate can be positioned to allow the bucket to rotate around the axles following application of the solution, as illustrated at 3406, and the rotor spun prior to positioning the stop plate to limit the spin angle, as illustrated at 3408. Such an additional spinning can assist with deposition of particles and beads into alignment with sensors of the sensor array, such as with deposition of particles or beads into wells associated with the sensors.

In one embodiment, a rotor assembly includes a rotor plate to rotate around a first axis, a bucket rotatably attached to the rotor plate and to rotate around a second axis, and a stop plate to rotate around the first axis relative to the rotor plate between an open position and a closed position, when in the closed position, the stop plate is to engage the bucket to fix an angular position of the bucket relative to a plane of rotation of the rotor assembly. The bucket can include a chamfered surface to engage the chamfered surface of the stop plate. In certain embodiments, the bucket can be weighted to provide an angular position relative to a plane of rotation of the rotor assembly when the rotor assembly is spinning. The rotor assembly further includes a housing for a sensor array component, the housing disposed in the bucket and including a transfer basin, a solution retainer adjacent to the transfer basin, and a collection reservoir in fluid communication with the transfer basin. The stop plate can include a wing with a chamfered surface to engage a surface of the bucket when the stop plate is moving to the closed position. In some embodiments, the stop plate can include an arm and a ring. The rotor plate can include an opening through which the ring of the stop plate can be accessed. The ring can include a chamfered slip.

The rotor assembly can further include a coupler having a central shaft to engage the rotor plate and the stop plate. The coupler can include a stop surface to engage a stop surface of the stop plate when the stop plate is in an open or closed position. In some embodiments, the coupler can include a magnet to attract a magnet of the stop plate when the stop plate is in an open or closed position. The rotor plate can include a recess with slots to receive the wings of the coupler to engage the slots of the rotor plate.

The rotor plate can include a top stop surface to engage the bucket or a sensor array component when the stop plate is in a closed position. Alternatively, the rotor plate can include a rear stop surface to engage the bucket when the stop plate is in a closed position.

In another embodiment, a method of loading a sensor array component includes applying a solution to a sensor array component located within a housing that includes a solution retainer, a transfer basin, and a collection reservoir disposed in a bucket of a rotor assembly when a stop plate of the rotor assembly is in a closed position. The method further includes spinning the rotor assembly, the bucket rotating to a horizontal or negative angle relative to the plane of rotation of the rotor assembly, the solution flowing over the retainer into the transfer basin, moving the stop plate to an open position, spinning the rotor assembly, the bucket rotating to a positive angle relative to a plane of rotation of the rotor assembly, the solution flowing from the transfer basin into the collection reservoir, and removing the solution from the collection reservoir. The rotor assembly can include a rotor plate to rotate around a first axis, a bucket rotatably attached to the rotor plate and to rotate around a second axis, and a stop plate to rotate around the first axis relative to the rotor plate between an open position and a closed position, when in the closed position, the stop plate is to engage the bucket to fix an angular position of the bucket relative to a plane of rotation of the rotor assembly.

In a first aspect, a fluid transfer housing to engage a sensor array having a flow cell includes a solution inlet and a solution outlet to engage ports of the flow cell; a transfer basin; a solution retainer disposed between the solution outlet and the transfer basin; and a collection reservoir in fluid communication with the transfer basin.

In a second aspect, a rotor assembly includes a rotor plate to rotate around a first axis; a bucket rotatably attached to the rotor plate and to rotate around a second axis; and a stop plate to rotate around the first axis relative to the rotor plate between an open position and a closed position. When in the closed position, the stop plate is to engage the bucket to fix an angular position of the bucket relative to a plane of rotation of the rotor assembly. The rotor assembly further includes a housing for a sensor array component. The housing is disposed in the bucket and includes a solution inlet, a solution outlet, a transfer basin, a solution retainer disposed between the solution outlet and the transfer basin, and a collection reservoir in fluid communication with the transfer basin. The solution inlet and the solution outlet engage ports of a flow cell of a sensor array.

In a third aspect, a method of loading a sensor array component includes applying a solution to a sensor array component located within a housing that includes a solution inlet, a solution outlet, a solution retainer, a transfer basin, and a collection reservoir disposed in a bucket of a rotor assembly when a stop plate of the rotor assembly is in a closed position. The method further includes spinning the rotor assembly, the bucket rotating to a horizontal or negative angle relative to a plane of rotation of the rotor assembly, and the solution flowing out of the fluid outlet, over the solution retainer, and into the transfer basin. The method also includes moving the stop plate to an open position and spinning the rotor assembly, the bucket rotating to a positive angle relative to the plane of rotation of the rotor assembly, the solution flowing from the transfer basin into the collection reservoir. The method optionally includes removing the solution from the collection reservoir.

In an example of the above aspects, the solution inlet has a conical opening to receive a distal end of a pipette tip.

In another example of the above aspects and the above examples, the solution inlet and the solution outlet further include gasket material to engage the ports of the flow cell.

In a further example of the above aspects and the above examples, the housing further includes a cap disposed over the transfer basin. For example, the cap can define an opening for accessing the solution outlet. In another example, the cap can define an opening for accessing the collection reservoir. In a further example, the housing further includes a fluid path defined between the cap and the solution retainer.

In an additional example of the above aspects and the above examples, when in a horizontal position and viewed from a side, the collection reservoir has a lower bottom than the transfer basin.

In another example of the above aspects and the above examples, when in a horizontal position and viewed from a side, the transfer basin has a bottom that is lower than the top of the solution retainer.

In a further example of the above aspects and the above examples, the transfer basin is positioned radially outwardly from the solution outlet and the solution retainer.

In an additional example of the above aspects and the above examples, the transfer basin is positioned radially outwardly from the collection reservoir.

In an example of the second aspect and the above examples, the stop plate includes a wing with a chamfered surface to engage a surface of the bucket when the stop plate is moving to the closed position. For example, the bucket includes a chamfered surface to engage the chamfered surface of the stop plate.

In another example of the second aspect and the above examples, the rotor plate includes a rear stop surface to engage the bucket when the stop plate is in a closed position.

In a further example of the second aspect and the above examples, the bucket is weighted to provide an angular position relative to a plane of rotation of the rotor assembly when the rotor assembly is spinning and the stop plate is in an open position.

In a further example of the above aspects and the above examples, the transfer basin is positioned radially outwardly from the solution outlet and the solution retainer relative to the first axis.

In an additional example of the above aspects and the above examples, the transfer basin is positioned radially outwardly from the collection reservoir relative to the first axis.

In an example of the third example and the above example, the rotor assembly includes a rotor plate to rotate around a first axis, a bucket rotatably attached to the rotor plate and to rotate around a second axis, and a stop plate to rotate around the first axis relative to the rotor plate between an open position and a closed position, when in the closed position, the stop plate is to engage the bucket to fix an angular position of the bucket relative to a plane of rotation of the rotor assembly.

In another example of the third aspect and the above examples, applying the solution includes applying the solution to the fluid inlet of the housing.

In a further example of the third aspect and the above examples, in response to spinning the rotor assembly with the bucket in the horizontal or negative angle, the solution flows through the flow cell to the solution outlet.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A rotor assembly comprising:
   a rotor plate to rotate around a first axis;
   a bucket rotatably attached to the rotor plate and to rotate around a second axis;
   a stop plate to rotate around the first axis relative to the rotor plate between an open position and a closed position, when in the closed position, the stop plate is to engage the bucket to fix an angular position of the bucket relative to a plane of rotation of the rotor assembly; and
   a housing for a sensor array component, the housing disposed in the bucket, the housing including a housing body defining:
   a solution inlet and a solution outlet to engage ports of a flow cell of a sensor array, the housing body defining a flow path beginning at the solution outlet;
   a transfer basin defined by the housing body and in the flow path;
   a solution retainer defined by the housing body and disposed between the solution outlet and the transfer basin within the flow path; and
   a collection reservoir defined by the housing body in fluid communication with the transfer basin within the flow path at an opposite end of the flow path from the solution retainer.

2. The rotor assembly of claim 1, wherein the stop plate includes a wing with a chamfered surface to engage a surface of the bucket when the stop plate is moving to the closed position.

3. The rotor assembly of claim 2, wherein the bucket includes a chamfered surface to engage the chamfered surface of the stop plate.

4. The rotor assembly of claim 1, wherein the rotor plate includes a rear stop surface to engage the bucket when the stop plate is in a closed position.

5. The rotor assembly of claim 1, wherein a weight of the bucket is distributed to provide an angular position relative to a plane of rotation of the rotor assembly when the rotor assembly is spinning and the stop plate is in an open position.

6. The rotor assembly of claim 1, wherein the solution inlet has a conical opening to receive a distal end of a pipette tip.

7. The rotor assembly of claim 1, wherein the solution inlet and the solution outlet further include gasket material to engage the ports of the flow cell.

8. The rotor assembly of claim 1, further comprising a cap coupled to the housing body and disposed over the transfer basin.

9. The rotor assembly of claim 8, wherein the cap defines an opening for accessing the solution outlet.

* * * * *